US008962662B2

(12) United States Patent
Busch et al.

(10) Patent No.: US 8,962,662 B2
(45) Date of Patent: Feb. 24, 2015

(54) ANTIMICROBIAL COMPOSITIONS AND METHODS OF USE THEREOF

(71) Applicant: Byocoat Enterprises, Inc., Guaynabo, PR (US)

(72) Inventors: Fredrick Busch, Clementon, NJ (US); Steve R. Burwell, Guaynabo, PR (US); Mark O'Reilly, San Francisco, CA (US)

(73) Assignee: Byocoat Enterprises, Inc., Guaynabo, PR (US)

( * ) Notice: Subject to any disclaimer, the term of this patent is extended or adjusted under 35 U.S.C. 154(b) by 0 days.

(21) Appl. No.: 13/675,155

(22) Filed: Nov. 13, 2012

(65) Prior Publication Data

US 2013/0137732 A1 May 30, 2013

Related U.S. Application Data

(60) Provisional application No. 61/559,882, filed on Nov. 15, 2011.

(51) Int. Cl.
*A01N 43/40* (2006.01)
*A01N 37/46* (2006.01)

(52) U.S. Cl.
CPC .............. *A01N 43/40* (2013.01); *A01N 37/46* (2013.01)
USPC ...................................... 514/358; 424/70.28

(58) Field of Classification Search
None
See application file for complete search history.

(56) References Cited

U.S. PATENT DOCUMENTS

| | | | |
|---|---|---|---|
| 4,737,307 A | 4/1988 | Brown et al. | |
| 5,366,983 A | 11/1994 | Lattin et al. | |
| 5,443,701 A | 8/1995 | Willner et al. | |
| 5,855,940 A | 1/1999 | Compadre et al. | |
| 5,906,825 A | 5/1999 | Seabrook, Jr. et al. | |
| 6,039,992 A | 3/2000 | Compadre et al. | |
| 6,086,863 A | 7/2000 | Ritter et al. | |
| 6,251,836 B1 | 6/2001 | Duncum et al. | |
| 6,464,971 B1 | 10/2002 | Matthews et al. | |
| 6,465,521 B1 | 10/2002 | Rosenberg | |
| 6,610,289 B2 | 8/2003 | Drake et al. | |
| 6,749,804 B2 | 6/2004 | Schneider et al. | |
| 6,846,420 B2 | 1/2005 | Reddy et al. | |
| 6,864,269 B2 | 3/2005 | Compadre et al. | |
| 6,976,647 B2 | 12/2005 | Reed et al. | |
| 7,018,834 B2 | 3/2006 | Drake et al. | |
| 7,101,576 B2 | 9/2006 | Hovey et al. | |
| 7,192,527 B2 | 3/2007 | Reddy | |
| 7,229,952 B2 | 6/2007 | Reddy et al. | |
| 7,320,963 B2 | 1/2008 | Esuvaranathan et al. | |
| 7,374,690 B2 | 5/2008 | Reddy | |
| 7,390,505 B2 | 6/2008 | Gustow et al. | |
| 7,459,283 B2 | 12/2008 | Wertz et al. | |
| 7,541,045 B2 | 6/2009 | Compadre et al. | |
| 7,572,459 B2 | 8/2009 | Matthews et al. | |
| 7,709,457 B2 | 5/2010 | Esuvaranathan et al. | |
| 8,057,774 B2 | 11/2011 | Kim et al. | |
| 8,075,936 B2 | 12/2011 | Burwell et al. | |
| 8,313,771 B2 | 11/2012 | Song et al. | |
| 8,323,641 B2 | 12/2012 | Wertz et al. | |
| 2001/0048916 A1 | 12/2001 | Kato et al. | |
| 2002/0064585 A1 | 5/2002 | Christianson et al. | |
| 2005/0069623 A1 | 3/2005 | Schneider et al. | |
| 2005/0271781 A1 | 12/2005 | Burwell et al. | |
| 2006/0083830 A1 | 4/2006 | Kemp et al. | |
| 2006/0110506 A1* | 5/2006 | Burwell et al. ............... | 426/335 |
| 2006/0257539 A1* | 11/2006 | Zheng et al. ................. | 426/335 |
| 2009/0186943 A1 | 7/2009 | Ikeda et al. | |
| 2009/0192165 A1 | 7/2009 | Burwell et al. | |
| 2009/0264340 A1 | 10/2009 | Choi et al. | |
| 2010/0055142 A1 | 3/2010 | Heagle et al. | |
| 2011/0015300 A1 | 1/2011 | Whiteford et al. | |

FOREIGN PATENT DOCUMENTS

| | | |
|---|---|---|
| CA | 2343113 C | 3/2000 |
| CA | 2750340 A1 | 7/2010 |
| GB | 1126953 A | 9/1968 |
| GB | 1384537 A | 2/1975 |
| GB | 2170713 A | 8/1986 |
| JP | H05219925 A | 8/1993 |
| JP | 06-256563 | 9/1994 |
| WO | 2006/017245 A2 | 2/2006 |

(Continued)

OTHER PUBLICATIONS

Baker, Zelma et al., "Action of Synthetic Detergents on the Metabolism of Bacteria," (From the Walter G. Zoller Memorial Dental Clinic, the Department of Bacteriology and Parasitology, and the Department of Medicine, The University of Chicago, Chicago) (Received for publication, Oct. 14, 1990) pp. 249-271.

Geornaras, I. et al., "Antimicrobial Activity of e-Polylysine against *Escherichia coli* O157:H7, *Salmonella typhimurium*, and *Listeria monocytogenes* in Various Food Extracts," Journal of Food Science, 72:M330-M334.

Shih, Ing-Lung et al., "Microbial synthesis of poly(e-lysine) and its various applications," Bioresource Technology 97 (2006) 1148-1159.

(Continued)

*Primary Examiner* — Melenie McCormick
*Assistant Examiner* — Taina D Matos Negron
(74) *Attorney, Agent, or Firm* — Sutherland Asbill & Brennan LLP

(57) ABSTRACT

This disclosure provides generally for antimicrobial compositions and methods for reducing or preventing microorganism growth, viability, or survival, which are useful for treating poultry, meat, seafood, vegetables, legumes, fruit, crops, and other products for human or animal consumption. For example, the compositions can include GRAS (Generally Recognized As Safe) antimicrobial components such as ε-poly-L-lysine in combination with at least one quaternary ammonium salt, including an aliphatic heteroaryl ammonium salt such as cetylpyridinium chloride.

14 Claims, 3 Drawing Sheets

(56) References Cited

FOREIGN PATENT DOCUMENTS

WO 2009/037269 A1 3/2009
WO 2010/083589 A1 7/2010

OTHER PUBLICATIONS

Shima, Shoji et al., "Antimicrobial Action of e-Poly-I-Lysine," The Journal of Antibiotics, vol. XXXVI, No. 11, Department of Agricultural Chemistry, College of Agriculture, University of Osaka Prefecture, Sakai, Osaka 591, Japan, (Received for publication Jan. 19, 1984), pp. 1449-1455.

Yoshida, T. et al., "e-Poly-I-Isine: microbial production, biodegradation and application potential," Appl Microbiol Biotechnol (2003), 62:21-26.

Mead, Paul S. et al., "Food-Related Illness and Death in the United States," Synopses, Emerging Infectious Diseases, vol. 5, No. 5, Sep.-Oct. 1999, pp. 607-625, Centers for Disease Control and Prevention, Atlanta, Georgia, USA.

Hinton, Jr., Arthur et al., "Bacterial Flora of Processed Broiler Chicken Skin after Successive Washings in Mixtures of Potassium Hydroxide and Lauric Acid," Journal of Food Protection, vol. 71, No. 8, 2008, pp. 1707-1713.

Annex to Form PCT/ISA/206, Communication Relating to the Results of the Partial International Search for PCT/US2012/064833, mailed May 29, 2013.

International Preliminary Report on Patentability for International Application No. PCT/US2012/064833, issued May 20, 2014.

* cited by examiner

ANTIMICROBIAL COMPOSITIONS AND METHODS OF USE THEREOF

CROSS-REFERENCE TO RELATED APPLICATIONS

This application claims the benefit of U.S. Provisional Application No. 61/559,882, filed Nov. 15, 2011, the disclosure of which is incorporated herein by reference in its entirety.

FIELD OF THE INVENTION

The disclosed matter generally relates to antimicrobial compositions and methods for reducing or preventing microorganism growth, viability, or survival that are useful for treating poultry, meat, seafood, vegetables, legumes, fruit, crops, and related products.

BACKGROUND OF THE INVENTION

Prevention of food-borne illness is of singular importance to the food industry, consumers, and government regulatory agencies. The Centers for Disease Control and Prevention (CDC) estimated in 2003 that food-borne diseases cause approximately 76 million illnesses, 325,000 hospitalizations, and 5,000 deaths in the U.S. each year (Mead, et al., Food-Related Illness and Death in the United States, Centers for Disease Control and Prevention, Atlanta, Ga., USA, 2003). The CDC report estimated that known pathogens account for an estimated 14 million illnesses, 60,000 hospitalizations, and 1,800 deaths, with *Salmonella, Listeria,* and *Toxoplasma* being responsible for about 1,500 deaths. Other food-borne microorganisms that are of public health concern include *Aeromonas hydrophile, Arcobacter butzleri, Bacillus cereus, Campylobacter jejuni, Escherichia coli,* and *Staphylococcus aureus*. The Center for Food Safety and Applied Nutrition of the Food and Drug Administration has estimated that the annual costs of food-borne illness in the U.S. is between $7.7 and $23 billion.

Many microorganisms can adhere to poultry, meat, seafood, vegetables, legumes, fruit, and other food tissues, making removal of the microorganisms difficult with rinsing alone. Consequently, treatments including irradiation, chemical treatment, and physical processing have been used to address the problem of microorganism contamination of food. However, the efficacy of many conventional treatments often is inconsistent, and compositions and methods that are effective against one type of microorganism are far less effective against other types. Presently, there are few known effective antimicrobial compositions that are useful against a broad range of microorganisms that can be safely be used on food surfaces.

As a result, there is a continuing need for new antimicrobial methods and compositions, which are effective in reducing or preventing microorganism growth, viability, or survival that can be applied to any type of potentially contaminated plant or animal products used for food. Desirably, the new methods and compositions can be applicable to poultry, meat, seafood, vegetables, legumes, fruit, and other food products for human or animal consumption. Further there is also a need for antimicrobial compositions that can be effectively be used on other surfaces, such as floors, coolers, tables, trays, and the like to reduce or substantially eliminate microbial contamination. Also desirably, a broad range of microorganisms can be substantially removed or diminished using the new methods and compositions.

SUMMARY OF THE INVENTION

In its various embodiments and aspects, this disclosure provides generally for compositions and methods for reducing or preventing microorganism growth, viability, or survival, which are particularly useful for treating poultry, meat, seafood, vegetables, legumes, fruit, and other products for human or animal consumption. For example, in some embodiments, the compositions can include ϵ-poly-L-lysine in combination with at least one quaternary ammonium salt, including an aliphatic heteroaryl ammonium salt such as cetylpyridinium chloride. In other embodiments, this disclosure provides for a method for reducing the number of microorganisms on a surface, comprising contacting a surface with a composition that can include ϵ-poly-L-lysine in combination with at least one quaternary ammonium salt. In this disclosure, ϵ-poly-L-lysine is alternatively referred to as epsilon-polylysine or EPL.

In one aspect, the disclosed matter relates generally to compositions and methods for preparing and using such compositions. Thus, in one aspect, the present disclosure provided for a composition comprising:
 a) at least one GRAS (generally recognized as safe) antimicrobial component; and
 b) at least one quaternary ammonium compound.

For example, the at least one GRAS (generally recognized as safe) component can be selected from ϵ-poly-L-lysine, Nisin, EDTA, alkyl polyglucoside, lactic acid, or any combination thereof. Substances that are generally recognized as safe by the U.S. Food and Drug Administration (FDA) are designated GRAS components, and such components can be used with or on food. Such GRAS components are exempted from the usual Federal Food, Drug, and Cosmetic Act (FFDCA) food additive tolerance restrictions. While any GRAS (generally recognized as safe) component can be employed that exhibits antimicrobial activity, this disclosure is generally illustrated with ϵ-poly-L-lysine, and most of the examples and disclosure refer to the use of ϵ-poly-L-lysine in combination with at least one quaternary ammonium compound.

In one aspect, for example, the present disclosure provides for an antimicrobial composition comprising:
 a) ϵ-poly-L-lysine; and
 b) at least one quaternary ammonium compound.

By way of example, the at least one quaternary ammonium compound can be selected independently from an aliphatic heteroaryl salt, an aliphatic benzyl dialkyl ammonium salt, a dialiphatic dialkyl ammonium salt, and a tetraalkyl ammonium salt.

Also by way of example, the antimicrobial composition can comprise:
 a) ϵ-poly-L-lysine; and
 b) one, two, or three quaternary ammonium compounds selected independently from an aliphatic heteroaryl salt, an aliphatic benzyl dialkyl ammonium salt, a dialiphatic dialkyl ammonium salt, and a tetraalkyl ammonium salt.

Further by way of example, the antimicrobial composition can comprise:
 a) ϵ-poly-L-lysine; and
 b) an aliphatic heteroaryl salt; and
 c) optionally, at least one additional quaternary ammonium compounds selected independently from an aliphatic benzyl dialkyl ammonium salt, a dialiphatic dialkyl ammonium salt, and a tetraalkyl ammonium salt.

In accordance with another aspect and embodiments of this disclosure, there is provided an antimicrobial composition comprising:
 a) ϵ-poly-L-lysine; and
 b) an aliphatic heteroaryl salt.

Preferred examples of the antimicrobial composition can comprise:

a) ε-poly-L-lysine; and
b) at least one of cetylpyridinium chloride and cetylpyridinium bromide.

In another aspect and in accordance with still other aspects and embodiments of this disclosure, there is provided an antimicrobial composition comprising:

a) a component having antimicrobial activity, consisting essentially of or alternatively comprising:
   i) ε-poly-L-lysine; and
   ii) an aliphatic heteroaryl salt;
   iii) at least one ammonium compound selected from an aliphatic benzyl dialkyl ammonium salt, a dialiphatic dialkyl ammonium salt, or a tetraalkyl ammonium salt; and
b) an aqueous carrier.

In yet another aspect and in other embodiments, there is provided an antimicrobial composition comprising:

a) a component having antimicrobial activity, consisting essentially of or alternatively comprising:
   i) ε-poly-L-lysine; and
   ii) an aliphatic heteroaryl salt; and
b) an aqueous carrier.

For example, preferred antimicrobial compositions can comprise:

a) a component having antimicrobial activity, consisting essentially of or alternatively comprising:
   i) ε-poly-L-lysine;
   ii) an aliphatic heteroaryl salt; and
   iii) one ammonium compound selected from an aliphatic benzyl dialkyl ammonium salt, a dialiphatic dialkyl ammonium salt, or a tetraalkyl ammonium salt, wherein the ammonium compounds not selected are not present; and
b) an aqueous carrier.

The present disclosure also provides for a method for reducing the number of microorganisms on a surface, comprising contacting a surface with any of the recited compositions.

BRIEF DESCRIPTION OF THE FIGURES

The accompanying figures, which are incorporated in and constitute a part of this specification, illustrate several aspects described below.

DETAILED DESCRIPTION OF THE INVENTION

Figure 1:
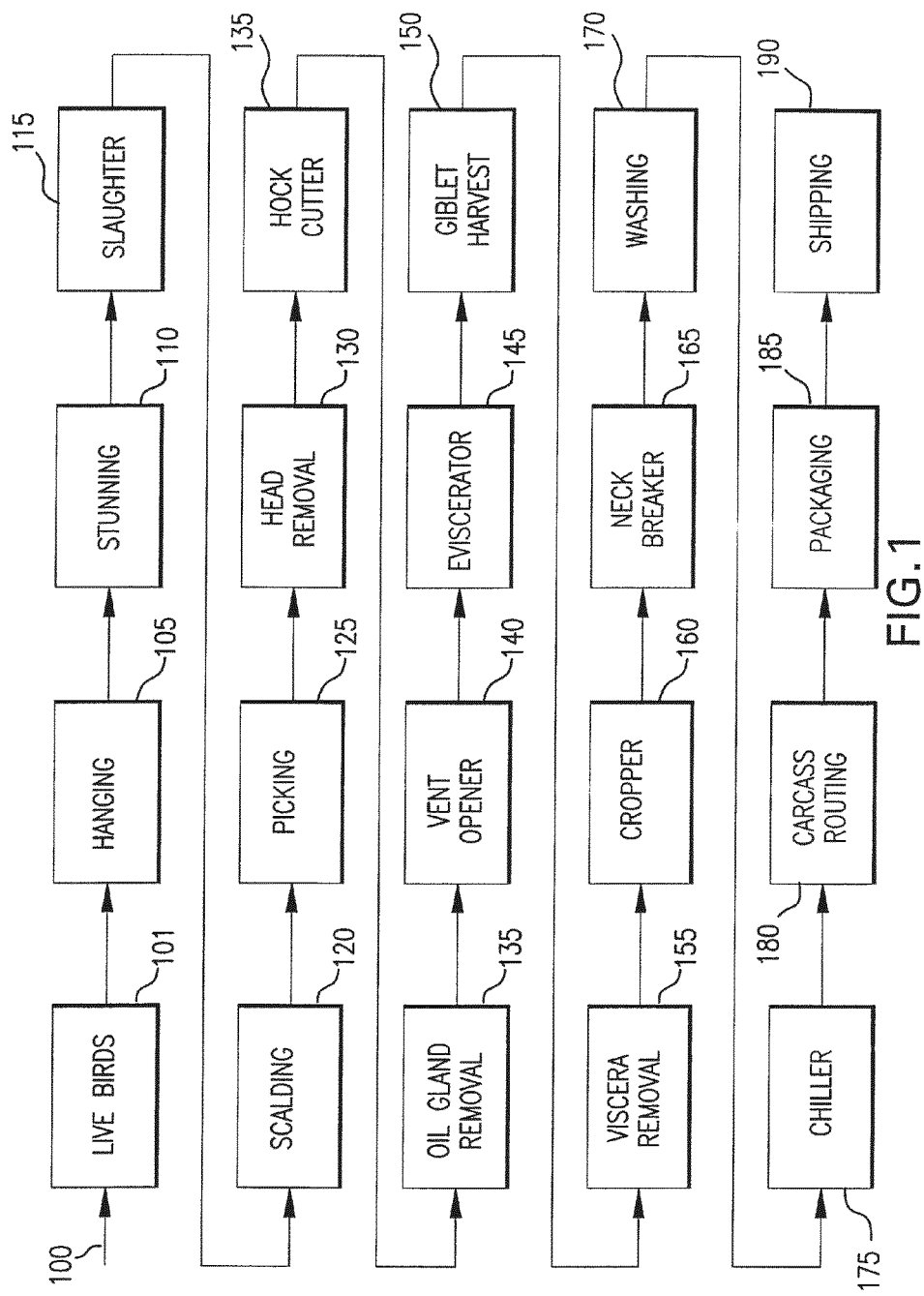
FIG. 1 is a flow chart showing the steps taken in poultry processing.

The materials, compositions, articles, devices, and methods described herein may be understood more readily by reference to the following detailed description of specific aspects of the disclosed subject matter, and methods and the Examples included therein and to the Figures and their previous and following description.

Before the present materials, compositions, articles, devices, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

A. Definitions

Unless otherwise indicated, the following definitions are applicable to this disclosure. If a term is used in this disclosure but is not specifically defined herein, the definition from the IUPAC Compendium of Chemical Terminology, $2^{nd}$ Ed (1997) can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls. Thus, in this specification and in the claims that follow, reference will be made to a number of terms, which shall be defined to have the following meanings:

As used in the specification and the appended claims, the singular forms "a," "an," and "the" include plural referents unless the context clearly dictates otherwise. Thus, for example, reference to "a compound" includes mixtures or combinations of two or more such compounds, reference to "an agent" includes mixtures of two or more such agents, reference to "the composition" includes mixtures of two or more such compositions, and the like.

Throughout the specification and claims, the word "comprise" and variations of the word, such as "comprising" and "comprises," means "including but not limited to," and is not intended to exclude, for example, other additives, components, integers, or steps.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Any references in the specification or claims to parts by weight of a particular element or component in a composition or article denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the composition or article.

A weight percent of a component, unless specifically stated to the contrary, is based on the total weight of the formulation or composition in which the component is included, according to its usual definition.

By "reduce" or other forms of the word, such as "reducing" or "reduction," is meant lowering of an event or characteristic (e.g., microorganism growth, viability, or survival). It is understood that this is typically in relation to some standard or expected value, in other words it is relative, but that it is not always necessary for the standard or relative value to be referred to. For example, "reduces the population of bacteria" means lowering the amount of bacteria relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, break-down, or eliminate a particular characteristic or event (e.g., microorganism growth, viability, or survival). It is generally understood that treating involves contacting the compositions disclosed herein with the surface, food product, poultry, meat, seafood, vegetables, legumes, fruit, or other material subject to treatment.

The term "substantially free", for example when describing a composition that is substantially free of a particular component, such as a compound or material, is meant to reflect that none of the recited component is intentionally added or used in the subject composition.

By "antimicrobial" is meant the ability to treat (e.g., reduce, prevent, inhibit, break-down, or eliminate) microorganism growth, viability, or survival at any concentration.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen and oxygen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with the normal rules of valence of the substituted atom and the substituent, and that the substitution results in a stable compound, e.g., a compound that does not spontaneously undergo transformation such as by rearrangement, cyclization, elimination, and the like. Also, as used herein "substitution" or "substituted with" is meant to encompass configurations where one substituent is fused to another substituent. For example, an aryl group substituted with an aryl group (or vice versa) can mean that one aryl group is bonded to the second aryl group via a single sigma bond and also that the two aryl groups are fused, e.g., two carbons of one alkyl group are shared with two carbons of the other aryl group.

The symbols "$A^1$," "$A^2$," "$A^3$," and "$A^4$" are used herein as generic symbols to represent various substituents. These symbols can be any substituent, not limited to those disclosed herein, and when they are defined to be certain specific substituents in one sentence, it is not intended to limit their definition in another sentence nor that they cannot be defined as some other substituents elsewhere in the disclosure.

The term "alkyl" as used herein is a branched or unbranched saturated hydrocarbon group of 1 to 40 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, octadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "alkyl halide" specifically refers to an alkyl group that is substituted with one or more halides, e.g., fluorine, chlorine, bromine, or iodine. When "alkyl" is used in one sentence and a specific term such as "alkyl halide" is used in another, it is not meant to imply that the term "alkyl" does not also refer to specific terms such as "alkyl halide" and the like.

This practice is also used for other groups described herein. That is, while a term such as "heteroaryl" refers to both unsubstituted and substituted heteroaryl moieties, the substituted moieties can, in addition, be specifically identified herein; for example, a particular substituted heteroaryl can be referred to as, e.g., an "alkyl heteroaryl." Similarly, a substituted alkenyl can be, e.g., an "alkenyl halide," and the like. Again, the practice of using a general term, such as "heteroaryl," and a specific term, such as "alkyl heteroaryl," is not meant to imply that the general term does not also include the specific term.

"Aliphatic benzylalkyl ammonium" salts or compounds refer to the class of quaternary compounds that include alkyl dimethyl benzyl ammonium chloride ("ADBAC"), containing a benzyl, methyl, and longer chain aliphatic (alkyl) groups bonded to the ammonium nitrogen. Generically, these compounds may be described to recite all the substituents on the quaternary nitrogen, for example, as aliphatic dialkyl benzyl ammonium compounds or aliphatic benzyl dialkyl ammonium compounds. Thus, the common usage of "aliphatic benzylalkyl ammonium" is used to encompass the quaternary ammonium compounds, as understood by one of ordinary skill.

The term "alkenyl" as used herein is a hydrocarbon group of from 2 to 40 carbon atoms with a structural formula containing at least one carbon-carbon double bond. Asymmetric structures such as $(A^1A^2)C=C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol.

The term "alkynyl" as used herein is a hydrocarbon group of 2 to 40 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol.

The term "aliphatic" as used herein refers to a non-aromatic hydrocarbon group and includes branched and unbranched alkyl, alkenyl, or alkynyl groups. Thus, aliphatic groups include alkyl groups. When the use of the term "aliphatic" is not accompanied with molecular fragment weight or carbon count or similar size limitations, no particular upper or lower size limit of the aliphatic group is intended.

The term "aryl" as used herein is a group that contains any carbon-based aromatic group including, but not limited to, benzene, benzyl, naphthalene, phenyl, biphenyl, phenoxybenzene, and the like. The term "aryl" also includes "heteroaryl," which is defined as a group that contains an aromatic group that has at least one heteroatom incorporated within the ring of the aromatic group. Examples of heteroatoms include, but are not limited to, nitrogen, oxygen, sulfur, and phosphorus. Likewise, the term "non-heteroaryl," which is also included in the term "aryl," defines a group that contains an aromatic group that does not contain a heteroatom. The aryl group can be substituted or unsubstituted. The aryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonylamino, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol.

The term "cycloalkenyl" as used herein is a non-aromatic carbon-based ring composed of at least three carbon atoms and contains at least one double bound, e.g., C=C. Examples of cycloalkenyl groups, include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, sulfo-oxo, sulfonylamino, nitro, silyl, or thiol.

The term "cyclic group" is used herein to refer to either aryl groups (e.g., heteraryl, biaryl), non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The terms "amine" or "amino" as used herein are represented by the formula:

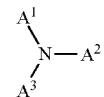

where $A^1$, $A^2$, and $A^3$ can each be, independent of one another, hydrogen, an alkyl, halogenated alkyl, alkenyl, alkynyl, aryl, heteroaryl, cycloalkyl, cycloalkenyl, heterocycloalkyl, or heterocycloalkenyl group described above. Also, any of the $A^1$, $A^2$, and $A^3$ substituents can be absent and any of the remaining substituents can be a multivalent group, i.e., form more than one bond with N.

The terms "ammonium" or "quaternary ammonium" are represented by the formula:

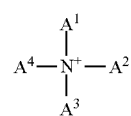

where $A^1$, $A^2$, $A^3$, and $A^4$ can each be, independent of one another, hydrogen, an alkyl, halogenated alkyl, alkenyl, alkynyl, aryl, heteroaryl, cycloalkyl, cycloalkenyl, heterocycloalkyl, or heterocycloalkenyl group described above. Also, any of the $A^1$, $A^2$, $A^3$, and $A^4$ substituents can be absent and any of the remaining substituents can be a multivalent group.

The terms polylysine, epsilon-polylysine, E-polylysine, ϵ-polylysine, E-poly-L-lysine, ϵ-poly-L-lysine, EPL, ϵ-PL, ϵPL, and the like are used interchangeably to refer to a homopolymer comprising L-lysine residues. This usage is used to refer to the small natural homopolymer of the essential amino acid L-lysine that is produced by bacterial fermentation. The epsilon (ϵ) refers to the linkage of the lysine molecules which, in contrast to normal peptide bond that is linked by the alpha-carbon group, the lysine amino acids are molecularly linked by the epsilon amino group and the carboxyl group. However, these terms also include homopolymers of L-lysine that may include one or more moieties that also includes a normal peptide bond, which may occur as a contaminant.

Unless the context requires otherwise, the term "halide" as used herein refers to the halogens fluorine, chlorine, bromine, or iodine in their covalent or ionic combined form. Thus, the term halide may be used to describe salt forms, such as an alkyl diethyl benzyl ammonium halide, but also may be used to describe covalently bonded halogens, such as "alkyl halide", as the context requires or allows.

The symbols "X," "$R^1$," "$R^2$," and "R," where n is some integer, as used herein can, independently, possess two or more of the groups listed above. For example, if R is a straight chain alkyl group, one of the hydrogen atoms of the alkyl group can optionally be substituted with a hydroxyl group (OH), an alkoxy group, halide, and the like. Depending upon the groups that are selected, a first group can be incorporated within second group or, alternatively, the first group can be pendant (i.e., attached) or fused to the second group.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixtures. The term "scalemic" may be used to describe any non-racemic chiral compound, and unless otherwise stated or the context requires otherwise, includes compounds that are "enantiopure" (enantiomerically pure) and/or "enantioenriched" (having an excess of one enantiomer but not to the exclusion of the other).

Reference will now be made in detail to specific aspects of the disclosed materials, compounds, compositions, components, devices, articles, and methods, examples of which are illustrated in the following description and examples, and in the figures and their previous and following description.

B. General Methods

Disclosed herein, in one aspect, are antimicrobial compositions. The disclosed antimicrobial compositions can be used to treat poultry, seafood, and meat tissue, as well as other foods such as fruits, vegetables, legumes, and the like against various microorganisms.

According to one aspect of this disclosure, there is provided an antimicrobial composition and a method for reducing the number of microorganisms on a surface, comprising contacting a surface with a composition, in which the subject composition comprises:

a) ϵ-poly-L-lysine;
b) at least one quaternary ammonium compound.

The ϵ-poly-L-lysine (ϵ-polylysine) used is not limited to a particular molecular weight or chain length. In some embodiments, the ϵ-polylysine can contain from about 20 to about 40 L-lysine residues. The preferred at least one quaternary ammonium compound is cetylpyridinium chloride or cetylpyridinium bromide.

In some aspects, each of the at least one quaternary ammonium compound is selected independently from an aliphatic heteroaryl salt, an aliphatic benzyl dialkyl ammonium salt, a dialiphatic dialkyl ammonium salt, and a tetraalkyl ammonium salt. When an aliphatic heteroaryl salt is included, it can be selected from, for example, cetylpyridinium chloride, cetylpyridinium bromide, or a combination thereof. When an aliphatic benzyl dialkyl ammonium salt is included, it can be selected from, for example, an alkyl dimethyl benzyl ammonium halide, alkyl diethyl benzyl ammonium halide, alkyl methylethyl benzyl ammonium halide, or a combination thereof. When a dialiphatic dialkyl ammonium salt is included, it can be selected from, for example, didodecyl dimethyl ammonium halide, dicetyl dimethyl ammonium halide, dilauryl dimethyl ammonium halide, dimyristyl dimethyl ammonium halide, distearyl dimethyl ammonium halide, diarachidyl dimethyl ammonium halide, and a combination thereof. When a tetraalkyl ammonium salt is included, it can be selected from, for example, cetyl trimethyl ammonium halide, lauryl trimethyl ammonium halide, myristyl trimethyl ammonium halide, stearyl trimethyl ammonium halide, arachidyl trimethyl ammonium halide, cetyl triethyl ammonium halide, or a mixture thereof. In a preferred aspect, the antimicrobial composition can comprise ϵ-poly-L-lysine and at least one of cetylpyridinium chloride and cetylpyridinium bromide.

In some embodiments, the polymer of L-lysine (ϵ-polylysine) and the total of the least one quaternary ammonium compound can be present in the composition in a weight ratio of about 500:1 to about 0.002:1, respectively. Alternatively, the ϵ-polylysine and the total of the least one quaternary ammonium compound can be present in the composition in a weight ratio of about 100:1 to about 0.01:1, respectively. The ϵ-polylysine and the total of the least one quaternary ammonium compound also can be present in the composition in a weight ratio of 10:1 to 0.1:1, respectively. Typically, the antimicrobial composition further includes water, and the ϵ-polylysine and the total of the least one quaternary ammonium compound are independently present in the composition in a weight percentage of from 0.01 wt % to 15 wt %.

Other components can be present in the composition, if desired. For example, the antimicrobial composition can also include at least one additive selected independently from a carrier, a diluent, an adjuvant, a solubilizing agent, a suspending agent, a surfactant, a secondary antimicrobial agent, a preservative, a filler, a viscosity modifier, a thixotropy modifier, an antifoaming agent, a wetting agent, an emulsifier, or any combinations thereof. For example, the disclosed antimicrobial composition can further comprise at least one surfactant selected from a cationic surfactant, an anionic surfactant, a non-ionic surfactant, and an amphoteric surfactant.

An additional aspect of this disclosure provides that antimicrobial composition is effective over a range of pH values. For example, the composition can be used when having a pH from about 4 to about 11. By way of example, the composition can have a pH from about 4 to about 11; alternatively, from about 5 to about 10; alternatively, from about 5.5 to about 9.5; alternatively, from about 6 to about 9.5; alternatively, from about 6.5 to about 9; alternatively, from about 6.5 to about 8.5; alternatively, from about 6.5 to about 8. There are no particular temperature limitations for use of the disclosed method and composition other than the practical limits associated with the particular application.

This disclosure also provides for a method comprising contacting a surface with an effective amount of the antimicrobial composition. By the term "effective amount" of a composition as provided herein is meant an amount of a composition sufficient to provide the desired result, e.g., reduction or prevention of microorganism growth, viability, or survival. As disclosed herein, the exact amount required will vary from use to use depending on a variety of processing parameters, as understood by one of ordinary skill, such as the type of surface, the type of microorganism to be treated, the size of the processing facilities (e.g., the volume of the scalder or chiller), the mode of application (e.g., electrospray or dipping), the particular compositions being used, and the like. Thus, the determination of what constitutes an "effective amount" can be made by routine testing with known concentrations and adjusting those concentrations as needed to obtain the desired result. Thus, an appropriate effective amount can be determined by one of ordinary skill in the art using only routine experimentation.

When the antimicrobial composition of this disclosure is applied to a surface to be treated, the antimicrobial composition generally can include a total amount of the combined ε-poly-L-lysine and at least one quaternary ammonium compound of about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 510, 520, 530, 540, 550, 560, 570, 580, 590, 600, 600, 610, 620, 630, 640, 650, 660, 670, 680, 690, 700, 700, 710, 720, 730, 740, 750, 760, 770, 780, 790, 800, 800, 810, 820, 830, 840, 850, 860, 870, 880, 890, 900, 900, 910, 920, 930, 940, 950, 960, 970, 980, 990, 1000, 1050, 1100, 1150, 1200, 1250, 1300, 1350, 1400, 1450, 1500, 1550, 1600, 1650, 1700, 1750, 1800, 1850, 1900, 1950, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5500, 6000, 6500, 7000, 7500, 8000, 8500, 9000, 9500, 10000, 20000, 30000, 40000, 50000, 60000, 70000, 80000, 90000, or 100000 parts per million (ppm) of the combined components, not including the aqueous carrier. Any of the stated values can form an upper or lower endpoint when appropriate. Other amounts are disclosed herein and other amounts of the individual components are disclosed herein.

C. Treatable Microorganisms

As disclosed herein, the antimicrobial compositions can be used to treat various surfaces to reduce, inhibit, prevent, disrupt, degrade, brake-down, eliminate, and the like, microorganism growth, viability, or survival. By "microorganism" or "microbe" is meant a single or multicelled organism, and can include one or more organisms of the same type or mixtures of organism. The microorganisms that can be treated by the compositions and methods disclosed herein can be Gram-positive or Gram-negative bacteria. Such bacteria can be pathogenic, indicator, and/or spoilage bacteria. In one aspect, the antimicrobial compositions disclosed herein can be used to treat microorganisms on surfaces or in aqueous environments.

The Gram-positive bacteria treatable by the compositions and methods disclosed herein can include, but are not limited to, *M. tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies *paratubercutosis, Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides*, and other *Nocardia* species, *Streptococcus viridans* group, *Peptococcus* species, *Peptostreptococcus* species, *Actinomyces israelii* and other *Actinomyces* species, *Propionibacterium acnes*, and *Enterococcus* species.

The Gram-negative bacteria treatable by the compositions and methods disclosed herein can include, but are not limited to, *Clostridium tetani, Clostridium perfringens, Clostridium botulinum*, other *Clostridium* species, *Pseudomonas aeruginosa*, other *Pseudomonas* species, *Campylobacter species, Vibrio cholerae, Ehrlichia* species, *Actinobacillus pleuropneumoniae, Pasteurella haemolytica, Pasteurella multocida*, other *Pasteurella* species, *Legionella pneumophila*, other *Legionella* species, *Salmonella typhi*, other *Salmonella* species, *Shigella* species *Brucella abortus*, other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi*, other *Hemophilus* species, *Yersinia pestis, Yersinia enterolitica*, other *Yersinia* species, *Escherichia coli, Escherichia hirae* and other *Escherichia* species, as well as other *Enterobacteriacae, Brucella abortus* and other *Brucella* species, *Burkholderia cepacia, Burkholderia pseudomallei, Francisella tularensis, Bacteroides fragilis, Fusobascterium nucleatum, Provetella* species, *Cowdria ruminantium, Klebsiella* species, and *Proteus species*.

The above examples of Gram-positive, Gram-negative, pathogenic, indicator, and spoilage bacteria are not intended to be limiting, but are intended to be representative of a larger population including all bacteria that effect public health, as well as non-Gram test responsive bacteria. Examples of other species of microorganisms include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Ajipia, Agrobacterium, Alcaligenes, Alloiococcus, Alteromonas, Amycolata, Amycolatopsis, Anaerobospirilhim, Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium, Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea, Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia*, and *Yokenella*.

In specific examples, the disclosed antimicrobial compositions can be used to treat the bacteria *Pseudomonas aeruginosa, Enterobacter aerogenes, Proteus vulgaris, Staphylococcus aureus, Bacillus cereus, Escherichia coli,* and *Legionella pneumophila*. Further, sulfur reducing bacteria can be problematic in oil field waters, and even in drinking water. Such sulfur reducing bacteria can be treated by the compositions and methods disclosed herein. Some specific, non-limiting examples of sulfur reducing bacteria that can be treated by the disclosed compositions and methods are species of the genera *Desulfovibrio, Desulfotomaculum, Desulfomonas, Desulfobulbus, Desulfobacter, Desulfococcus, Desulfonema, Desulfosarcina, Desulfobacterium,* and *Desulforomas*.

The disclosed antimicrobial compositions can be used to treat other microorganisms such as, for example, parasites. Examples of parasites that can be treated include, but are not limited to, *Toxoplasma gondii, Plasmodium* species such as *Plasmodium falciparum, Plasmodium vivax, Plasmodium malariae,* and other *Plasmodium* species, *Trypanosoma brucei, Trypanosoma cruzi, Leishmania* species such as *Leishmania major, Schistosoma* such as *Schistosoma mansoni* and other *Shistosoma* species, and *Entamoeba histolytica*.

D. Compositions And Components

Disclosed herein, in one aspect, are antimicrobial compositions and methods. The disclosed antimicrobial compositions can be used to eliminate, reduce, and/or prevent microorganism growth, viability, or survival.

In some embodiments and aspects, the disclosed antimicrobial composition can comprise E-polylysine and an aliphatic heteroaryl ammonium compound such as cetylpyridinium chloride, cetylpyridinium bromide, or a combination thereof.

In other embodiments and aspects, the disclosed antimicrobial composition can comprise an aliphatic benzyl dialkyl ammonium salt (e.g., alkyldimethylbenzalkonium halide) and E-polylysine.

In still other embodiments and aspects, the disclosed antimicrobial composition can comprise E-polylysine; an aliphatic heteroaryl ammonium compound such as cetylpyridinium chloride, cetylpyridinium bromide, or a combination thereof; and an aliphatic benzyl dialkyl ammonium salt such as alkyl dimethyl benzyl ammonium chloride (ADBAC).

1. Homopolymer Comprising L-Lysine Residues

According to one aspect of this disclosure, the antimicrobial composition can comprise E-polylysine and at least one quaternary ammonium salt. E-Polylysine is a naturally produced homopolymer or oligomer that typically contains about 20 to 40 or so L-lysine residues that is produced by bacterial fermentation in strains of *Streptomyces*. ε-Polylysine is edible, non-toxic to humans, and water soluble. Moreover, EPL is also stable at relatively high temperatures, making it useful in poultry processing even when used in scalder water. A general structure of E-polylysine is illustrated here.

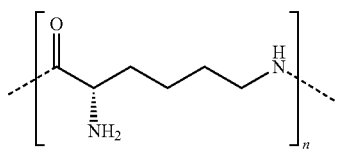

According to one aspect of this disclosure, E-polylysine in combination with the quaternary ammonium compounds described herein impart a preservative effect on the food tissue after processing, and therefore the disclosed compositions can be retained on the food tissue to increase the shelf life of the product. This feature can be advantageous for reducing or preventing microorganism growth, viability, or survival for a broad range of microorganisms.

The E-polylysine disclosed herein can be prepared by methods known in the art or can be obtained from commercial sources. The amounts of this component that can be used in the disclosed compositions are provided hereinbelow.

2. Aliphatic Heteroaryl Salt

According to one aspect, the antimicrobial composition can comprise at least one quaternary ammonium salt or compound that contains at least one heteroaryl group. According to another aspect, the quaternary ammonium salt can comprise or can be selected from an aliphatic heteroaryl salt, also referred to herein as an aliphatic heteroaryl ammonium salt or compound.

In accordance with this aspect, the disclosed antimicrobial compositions can comprise an aliphatic heteroaryl salt (e.g., one or more aliphatic heteroaryl salts). An aliphatic heteroaryl salt is a compound that comprises an aliphatic moiety bonded to a heteroaryl moiety, and a counterion, as are defined herein. One or more types of aliphatic heteroaryl salts can be used in the antimicrobial compositions disclosed herein.

Aliphatic Moiety

In the aliphatic heteroaryl salt component of the disclosed antimicrobial compositions, the aliphatic moiety can be any alkyl, alkenyl, alkynyl, cycloalkyl, or cycloalkenyl group, as described herein. Generally, the aliphatic moiety can comprise at least 10, at least 12, at least 14, at least 16, at least 18, or at least 20 carbon atoms. In other examples, the aliphatic moiety can comprise a mixture of aliphatic groups having a range of carbon atoms. For example, the aliphatic moiety can comprise from 10 to 40, from 12 to 38, from 14 to 36, from 16 to 34, from 18 to 32, from 14 to 18, or from 20 to 30 carbon atoms. In some specific examples, the aliphatic moiety can contain 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 carbon atoms, where any of the stated values can form an upper or lower endpoint when appropriate. Examples of specific aliphatic moieties that can be used in the disclosed aliphatic heteroaryl salts include, but are not limited to, decyl, dodecyl (lauryl), tetradecyl (myristyl), hexadecyl (palmityl or cetyl), octadecyl (stearyl), eicosyl (arachidyl), and linolenyl groups, including branched derivatives thereof and any mixtures thereof. In the aliphatic heteroaryl salts, the aliphatic moiety is bonded to a heteroatom in the heteroaryl moiety.

Heteroaryl Moiety

In the aliphatic heteroaryl salt component of the disclosed antimicrobial compositions, the heteroaryl moiety can be any heteroaryl moiety as described herein. For example, the heteroaryl moiety can be an aryl group having one or more heteroatoms. Examples of specific heteroaryl moieties that can be used in the aliphatic heteroaryl salts include, but are not limited to, pyrazole, pyridine, pyrazine, pyrimidine, pryidazine, indolizine, isoindole, indole, indazole, imidazole, oxazole, triazole., thiazole, purine, isoquinoline, quinoline, phthalazine, quinooxaline, phenazine, and the like, including substituted derivatives and mixtures thereof.

In the aliphatic heteroaryl salts, a heteroatom in the heteroaryl moiety is bonded to the aliphatic moiety. When the heteroatom is nitrogen, this forms a quaternary ammonium species.

Counterion

In the disclosed aliphatic heteroaryl salts, the counterion can be any ion that has an opposite charge as the remaining aliphatic heteroaryl portion of the salt. For example, when the heteroatom of heteroaryl moiety is bonded to the aliphatic moiety to form a positively charged quaternary ammonium moiety, the counterion can be a negatively charged moiety. Likewise, if the aliphatic heteroaryl portion is negatively charged, then the counterion can be positively charged. In the disclosed aliphatic heteroaryl salts, one or more different types of counterions can be present.

In some specific examples, the counterion can be a halide, such as a fluoride, chloride, bromide, or iodide. In other examples, suitable counterions for the aliphatic heteroaryl salt can include, but are not limited to, sulfide, sulfates, sulfites, phosphide, phosphates, phosphites, carbonates, bicarbonates, nitrates, nitrites, hypochlorite, chlorite, perchlorate, acetate, formate, hydroxide, and the like, including mixtures thereof.

Specific Examples

In one aspect, the aliphatic heteroaryl salt can have any of the aliphatic moieties disclosed above combined with any of the heteroaryl moieties disclosed above. In some specific examples, the aliphatic heteroaryl salt can be an alkyl pyridinium salt, an alkyl quinolinium salt, an alkyl imidazolinium salt, or any mixture thereof. In other examples, the aliphatic heteroaryl salt can be an alkenyl pyrazolium salt, an alkenyl pyrazinium salt, an alkenyl quinolinium salt, or any mixture thereof. The counter ions for these specific examples can be halides, nitrates, sulfates, carbonates or any other counterion disclosed herein. In other aspects, a specific example of an alkyl pyridinium salt includes an alkyl pyridinium halide such as, but not limited to, cetylpyridinium halide (e.g., cetylpyridinium chloride, cetylpyridinium bromide, or mixtures thereof), laurylpyridinium halide (e.g., laurylpyridinium chloride, laurylpyridinium bromide, or mixtures thereof), myristylpyridinium halide (e.g., myristylpyridinium chloride, myristylpyridinium bromide, or mixtures thereof), stearylpyridinium halide (e.g., stearylpyridinium chloride, stearylpyridinium bromide, or mixtures thereof), and arachidylpyridinium halide (arachidylpyridinium chloride, arachidylpyridinium bromide, or mixtures thereof). In a specific example, the aliphatic heteroaryl salt can comprise cetylpyridinium chloride, cetylpyridinium bromide, or a mixture thereof.

The aliphatic heteroaryl salt disclosed herein can be prepared by methods known in the art or can be obtained from commercial sources. The amounts of this component that can be used in the disclosed compositions are provided hereinbelow.

3. Aliphatic Benzyl Dialkyl Ammonium Salt

According to one aspect, the high pH-triggered component and the pH-triggered composition contains art least one quaternary ammonium salt that activates at about pH 7 or higher. In one aspect, the quaternary ammonium salt can contain at least one aryl or heteroaryl group that activates at about pH 7 or higher. According to another aspect, the quaternary ammonium salt can comprise or can be selected from an aliphatic benzyl dialkyl ammonium salt.

The disclosed antimicrobial compositions can comprise an aliphatic benzyl dialkyl ammonium salt (e.g., one or more aliphatic benzylakyl ammoniums salts). An aliphatic benzyl dialkyl ammonium salt is a compound that comprises an aliphatic moiety bonded to the nitrogen atom of a benzylalkyl amine moiety, and a counterion, as are defined herein. The aliphatic moiety and counterion can be as described above. The benzylalkyl amine moiety can be a benzyl amine where the amine is bonded to an alkyl or cyclic alkyl group, as described above. One or more types of aliphatic benzyl dialkyl ammonium salts can be used in the antimicrobial compositions disclosed herein. The aliphatic benzyl dialkyl ammonium salts suitable for use herein can be prepared by methods known in the art or can be obtained from commercial sources.

In one aspect, the aliphatic benzyl dialkyl ammonium salt can be represented by the following formula:

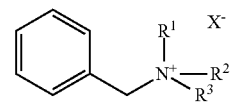

wherein $R^1$ is an aliphatic group, as described above, $R^2$ and $R^3$ are, independent of one another, alkyl groups or cyclic alkyl groups as described herein, and X is a counterion as described herein. In some examples, one or more of the "R" substituents can be a long chain alkyl group (e.g., the number of carbon atoms is greater than 6). In other examples, one or more of the "R" substituents can be a short chain alkyl group (e.g., the number of carbon atoms is 6 or less). In still other examples, one of the "R" substituents is a long chain alkyl group and the other two "R" substituents are short chain alkyl groups.

Specific Examples

In one aspect, the aliphatic benzyl dialkyl ammonium salt can have any of the aliphatic moieties disclosed above bonded to any benzylalkyl amine moieties disclosed above. In some specific examples, $R^1$ in the formula of aliphatic benzyl dialkyl ammonium salts can be an aliphatic group of from 10 to 40 carbon atoms, e.g., a decyl, dodecyl (lauryl), tetradecyl (myristyl), hexadecyl (palmityl or cetyl), octadecyl (stearyl), or eicosyl (arachidyl) group, and R and R can each be, independent of one another, a methyl, ethyl, propyl, butyl, pentyl, or hexyl group.

In another aspect, the aliphatic benzyl dialkyl ammonium salts can include, but are not limited to, alkyl dimethyl benzyl ammonium halides (e.g., alkyl dimethyl benzyl ammonium chloride, alkyl dimethyl benzyl ammonium bromide, or mixtures thereof). Specific examples of alkyl dimethyl benzyl ammonium halides include, but are not limited to, cetyl dimethyl benzyl ammonium halide (e.g., cetyl dimethyl benzyl ammonium chloride, cetyl dimethyl benzyl ammonium chloride bromide, or mixtures thereof), lauryl dimethyl benzyl ammonium halide (e.g., lauryl dimethyl benzyl ammonium chloride, lauryl dimethyl benzyl ammonium bromide, or mixtures thereof), myristyl dimethyl benzyl ammonium halide (e.g., myristyl dimethyl benzyl ammonium chloride, myristyl dimethyl benzyl ammonium bromide, or mixtures thereof), stearyl dimethyl benzyl ammonium halide (e.g., stearyl dimethyl benzyl ammonium chloride, stearyl dimethyl benzyl ammonium bromide, or mixtures thereof), and arachidyl dimethyl benzyl ammonium halide (e.g., arachidyl dimethyl benzyl ammonium chloride, arachidyl dimethyl benzyl ammonium bromide, or mixtures thereof).

In yet another aspect, the aliphatic benzyl dialkyl ammonium salts can include, but are not limited to, alkyl methylethyl benzyl ammonium halides. Specific examples of alkyl methylethyl benzyl ammonium halides include, but are not limited to, cetyl methylethyl benzyl ammonium halide (e.g., cetyl methylethyl benzyl ammonium chloride, cetyl methylethyl benzyl ammonium chloride bromide, or mixtures thereof), lauryl methylethyl benzyl ammonium halide (e.g., lauryl methylethyl benzyl ammonium chloride, lauryl methylethyl benzyl ammonium bromide, or mixtures thereof), myristyl methyl ethyl benzyl ammonium halide (e.g., myristyl methylethyl benzyl ammonium chloride, myristyl methylethyl benzyl ammonium bromide, or mixtures thereof), stearyl methylethyl benzyl ammonium halide (e.g., stearyl methylethyl benzyl ammonium chloride, stearyl methylethyl benzyl ammonium bromide, or mixtures thereof), and arachidyl methylethyl benzyl ammonium halide (e.g., arachidyl methylethyl benzyl ammonium chloride, arachidyl methylethyl benzyl ammonium bromide, or mixtures thereof).

Aliphatic benzyl dialkyl ammonium salts with ε-polylysine are particularly preferred compositions.

The aliphatic benzyl dialkyl ammonium salt disclosed herein can be prepared by methods known in the art or can be obtained from commercial sources. The amounts of this component that can be used in the disclosed compositions are provided hereinbelow.

4. Dialiphatic Dialkyl Ammonium Salts

The disclosed antimicrobial compositions can comprise a dialiphatic dialkyl ammonium salt (e.g., one or more dialiphatic dialkyl ammonium salts). A dialiphatic dialkyl ammonium salt is a compound that comprises two aliphatic moieties and two alkyl moieties bonded to a nitrogen atom, and a counterion, as are defined herein. The aliphatic moieties can be the same or different and can be any aliphatic group as described above. The alkyl moieties can be the same or different can be any alkyl group as described above. The counterion can also be as described above. In the disclosed dialiphatic dialkyl ammoniums salts, the two aliphatic moieties can have more than 10 carbon atoms and the two alkyl moieties can have less than 10 carbon atoms. In another alternative, the two aliphatic moieties can have less than 10 carbon atoms and the two alkyl moieties can have more than 10 carbon atoms. One or more types of dialiphatic dialkyl ammonium salts can be used in the antimicrobial compositions disclosed herein.

In some particular examples, the dialiphatic dialkyl ammonium salt can be di-dodecyl dimethyl ammonium chloride or bromide, di-tetradecyl dimethyl ammonium chloride or bromide, dihexadecyl dimethyl ammonium chloride or bromide, and the like, including combinations thereof.

The dialiphatic dialkyl ammonium salt disclosed herein can be prepared by methods known in the art or can be obtained from commercial sources. The amounts of this component that can be used in the disclosed compositions are provided hereinbelow.

5. Tetraalkyl Ammonium Salts

The disclosed antimicrobial compositions can also comprise a tetraalkyl ammonium salt (e.g., one or more tetraalkyl ammonium salts). Suitable tetraalkyl ammonium salts comprise four alkyl moieties, as disclosed herein, and a counterion, also disclosed herein. In one example, a tetraalkyl ammonium salt can comprise one long chain alkyl moiety (e.g., greater than 10 carbon atoms in length) and three short chain alkyl moieties (e.g., 10 carbon atoms or less in length).

Some specific examples of tetraalkyl ammonium salts that can be included in the disclosed antimicrobial compositions include, but are not limited to, cetyl trimethyl ammonium halide (e.g., chloride or bromide), lauryl trimethyl ammonium halide (e.g., chloride or bromide), myristyl trimethyl ammonium halide (e.g., chloride or bromide), stearyl trimethyl ammonium halide (e.g., chloride or bromide), arachidyl trimethyl ammonium halide (e.g., chloride or bromide), or mixtures thereof. Other examples include, but are not limited to, cetyl dimethylethyl ammonium bromide, lauryl dimethylethyl ammonium chloride, lauryl dimethylethyl ammonium bromide, myristyl dimethylethyl ammonium chloride, myristyl dimethylethyl ammonium bromide, stearyl dimethylethyl ammonium chloride, stearyl dimethylethyl ammonium bromide, arachidyl dimethylethyl ammonium chloride, arachidyl dimethylethyl ammonium bromide, or mixtures thereof.

The tetraalkyl ammonium salt disclosed herein can be prepared by methods known in the art or can be obtained from commercial sources. The amounts of this component that can be used in the disclosed compositions are provided hereinbelow.

6. Amounts of Each Component in the Composition

As disclosed, the antimicrobial composition can comprise ε-poly-L-lysine and at least one quaternary ammonium compound, wherein each of the at least one quaternary ammonium compound is selected independently from an aliphatic heteroaryl salt, an aliphatic benzyl dialkyl ammonium salt, a dialiphatic dialkyl ammonium salt, and a tetraalkyl ammonium salt. The preferred quaternary ammonium compound is at least one aliphatic heteroaryl salt. Typically, the composition is an aqueous composition that comprises the ε-poly-L-lysine and the at least one quaternary ammonium compound, and in the following discussion of amounts, the amounts recited are applicable to each component individually, regardless of how many components may be present in that particular antimicrobial composition. Therefore, reference to a component and an amount of a component in this section means any one of the ε-poly-L-lysine, aliphatic heteroaryl salt, aliphatic benzyl dialkyl ammonium salt, dialiphatic dialkyl ammonium salt, and tetraalkyl ammonium salt in the composition. These are typically aqueous solutions of the components, but these amounts refer to the concentrations in any composition they are used in.

Each of the recited components can be present in the antimicrobial compositions disclosed herein in an amount of from less than about 25 weight %, less than about 20 weight %, less than about 15 weight %, less than about 10 weight %, less than about 8 weight %, less than about 6 weight %, less than about 5 weight %, less than about 4 weight %, less than about 3 weight %, less than about 2 weight %, less than about 1 weight %, less than about 0.5 weight %, less than about 0.1 weight %, less than about 0.05 weight %, less than about 0.01 weight %, less than about 0.005 weight %, or less than about 0.001 weight %. based on the total weight of the antimicrobial composition. In another aspect, each component can be present in the antimicrobial compositions disclosed herein in an amount of from greater than about 0.001 weight %, greater than about 0.005 weight %, greater than about 0.01 weight %, greater than about 0.05 weight %, greater than about 0.1 weight %, greater than about 0.5 weight %, greater than about 1 weight %, greater than about 2 weight %, greater than about 3 weight %, greater than about 4 weight %, greater than about 5 weight %, greater than about 6 weight %, greater than about 8 weight %, greater than about 10 weight %, greater than about 15 weight %, greater than about 20 weight %, or greater than about 25 weight %, based on the total weight of the antimicrobial composition. In still another aspect, each component can be present in the antimicrobial compositions disclosed herein in an amount of from about 0.001 to about 25 weight %, from about 0.01 to about 22.5 weight %, from about 0.1 to about 20 weight %, from about 0.5 to about 18.5 weight %, from about 1 to about 15 weight %, from about 2 to about 12 weight %, from about 3 to about 10 weight %, or from about 4 to about 8 weight %, based on the total weight of the antimicrobial composition. In yet another aspect, each component can be present in the antimicrobial compositions disclosed herein in an amount of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25. 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.5, 16.75, 17.0, 17.25, 17.5, 17.75, 18.0, 18.25, 18.5, 18.75, 19.0, 19.25, 19.5, 19.75, 20.0, 21.25, 21.5, 21.75, 22.0, 22.25, 22.5, 22.75, 23.0, 23.25, 23.5, 23.75, 24.0, 24.25, 24.5, 24.75, or 25.0 weight %, based on the total weight of the antimicrobial composition and where any of the stated values can form an upper or lower endpoint when appropriate. Thus, this disclosure includes any range or combinations of ranges or sub-ranges between and including these values when appropriate.

In another aspect, the antimicrobial compositions disclosed herein can contain less than about 25 parts by weight, less than about 20 parts by weight, less than about 15 parts by weight, less than about 10 parts by weight, less than about 8 parts by weight, less than about 6 parts by weight, less than about 5 parts by weight, less than about 4 parts by weight, less than about 3 parts by weight, less than about 2 parts by weight, less than about 1 parts by weight, less than about 0.5 parts by weight, less than about 0.1 parts by weight, less than about 0.05 parts by weight, less than about 0.01 parts by weight, less than about 0.005 parts by weight, or less than about 0.001 parts by weight of each component based on the total weight of the antimicrobial composition. In another aspect, each component can be present in the antimicrobial compositions disclosed herein in an amount of from greater than about 0.001 parts by weight, greater than about 0.005 parts by weight, greater than about 0.01 parts by weight, greater than about 0.05 parts by weight, greater than about 0.1 parts by weight, greater than about 0.5 parts by weight, greater than about 1 parts by weight, greater than about 2 parts by weight, greater than about 3 parts by weight, greater than about 4 parts by weight, greater than about 5 parts by weight, greater than about 6 parts by weight, greater than about 8 parts by weight, greater than about 10 parts by weight, greater than about 15 parts by weight, greater than about 20 parts by weight, or greater than about 25 parts by weight, based on the total weight of the antimicrobial composition. In still another aspect, each component can be present in the antimicrobial compositions disclosed herein in an amount of from about 0.001 to about 25 parts by weight, from about 0.01 to about 22.5 parts by weight, from about 0.1 to about 20 parts by weight, from about 0.5 to about 18.5 parts by weight, from about 1 to about 15 parts by weight, from about 2 to about 12 parts by weight, from about 3 to about 10 parts by weight, or from about 4 to about 8 parts by weight, based on the total weight of the antimicrobial composition. In yet another aspect, each component can be present in the antimicrobial compositions disclosed herein in an amount of about 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.25, 1.5, 1.75, 2.0, 2.25, 2.5, 2.75, 3.0, 3.25, 3.5, 3.75, 4.0, 4.25, 4.5, 4.75, 5.0, 5.25, 5.5, 5.75, 6.0, 6.25, 6.5, 6.75, 7.0, 7.25, 7.5, 7.75, 8.0, 8.25, 8.5, 8.75, 9.0, 9.25, 9.5, 9.75, 10.0, 10.25. 10.5, 10.75, 11.0, 11.25, 11.5, 11.75, 12.0, 12.25, 12.5, 12.75, 13.0, 13.25, 13.5, 13.75, 14.0, 14.25, 14.5, 14.75, 15.0, 15.25, 15.5, 15.75, 16.0, 16.25, 16.5, 16.75, 17.0, 17.25, 17.5, 17.75, 18.0, 18.25, 18.5, 18.75, 19.0, 19.25, 19.5, 19.75, 20.0, 21.25, 21.5, 21.75, 22.0, 22.25, 22.5, 22.75, 23.0, 23.25, 23.5, 23.75, 24.0, 24.25, 24.5, 24.75, or 25.0 parts by weight, based on the total weight of the antimicrobial composition and where any of the stated values can form an upper or lower endpoint when appropriate. Thus, this disclosure includes any range or combinations of ranges or sub-ranges between and including these values when appropriate.

In another aspect, for example, the antimicrobial compositions that contain each component at an individual concentration of about 20, 50, 100, 150, 200, 250, 300, 350, 400, 450, 500, 550, 600, 650, 700, 750, 800, 850, 900, 950, 1000, 1250, 1500, 1750, 2000, 2500, 3000, 3500, 4000, 4500, 5000, 5500, 6000, 6500, 7000, 7500, 8000, 8500, 9000, 10000, 20000, 30000, 40000, 50000, 60000, 70000, 80000, 90000, or 100000 ppm, in the composition, where any of the stated values can form an upper or lower endpoint when appropriate. In some particular aspects, the disclosed compositions are suitable at concentrations of from about 100 ppm to about 1000 ppm.

7. Other Components

In addition to the components disclosed above, the disclosed antimicrobial compositions can be in the form of an aqueous solution, thus, water can be another component of the disclosed compositions. Also, the disclosed antimicrobial compositions can optionally include one or more additives such as carriers, adjuvants, solubilizing agents, suspending agents, diluents, surfactants, other antimicrobial agents, preservatives, fillers, wetting agents, antifoaming agents, emulsifiers, and additives designed to affect the viscosity, thixotropy or ability of the antimicrobial composition to adhere to and/or penetrate tissue. In one aspect, the one or more of the additives can be consumer acceptable. By "consumer acceptable" is meant a material that is not biologically or otherwise undesirable when consumed, e.g., an agent that is acceptable when used in or on foods and beverages and which can be consumed by an individual (e.g., human, pet, livestock, etc.) along with the selected active components without causing significant undesirable biological effects or interacting in a deleterious manner with any of the other components of the composition in which it is contained. For example, a consumer acceptable agent can be any compound generally recognized as safe (GRAS). These additives can be prepared by methods known in the art or obtained from commercial sources.

In one example, suitable additives include surfactants such as Triton X-100 (i.e., polyethylene glycol p-1,1,3,3-tetramethylbutylphenyl ether) for better cell penetration.

Carriers

In other examples, the antimicrobial compositions disclosed herein can further comprise a carrier. The term "carrier" means a compound, composition, substance, or structure that, when in combination with a compound or composition disclosed herein, aids or facilitates preparation, storage, administration, delivery, effectiveness, selectivity, or any other feature of the compound or composition for its intended use or purpose. For example, a carrier can be selected to minimize any degradation of the active components and to minimize any adverse side effects. Examples of suitable aqueous and non-aqueous carriers, diluents, solvents include water, ethanol, polyols (propyleneglycol, polyethyleneglycol, glycerol, and the like), vegetable oils, and suitable mixtures thereof.

Adjuvants

In a further example, the antimicrobial compositions disclosed herein can also comprise adjuvants such as preserving, wetting, emulsifying, suspending agents, flocculating, and dispensing agents. Prevention of the action of other microorganisms can be accomplished by various antifungal agents, for example, parabens, chlorobutanol, phenol, sorbic acid, and the like. It may also be desirable to include surfactants, binders, as for example, carboxymethylcellulose, alignates, gelatin, polyvinylpyrrolidone, sucrose, and acacia, humectants, as for example, glycerol, wetting agents, as for example, cetyl alcohol, and glycerol monostearate, adsorbents, as for example, kaolin and bentonite, and lubricants, as for example, talc, calcium stearate, magnesium stearate, solid polyethylene glycols, sodium lauryl sulfate, or mixtures thereof. Suitable flocculating agents that can be used include, but are not limited to, aluminum salts (e.g., aluminium sulphate), ferrous salts, and ferric salts (e.g., ferric sulphate and ferric chloride).

Solubilizing and Suspending Agents

Suitable suspending agents can include, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

The disclosed antimicrobial compositions can also comprise solubilizing agents and emulsifiers, as for example, ethyl alcohol, isopropyl alcohol, ethyl carbonate, ethyl acetate, benzyl alcohol, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydro fur fury 1 alcohol, polyethyleneglycols and fatty acid esters of sorbitan or mixtures of these substances, and the like.

Additional Quaternary Ammonium Salts

In one aspect, the disclosed antimicrobial compositions can comprise one or more additional quaternary ammonium salts. Other additional quaternary ammonium salts that can be used in the disclosed antimicrobial compositions include, but are not limited to, other aliphatic heteroaryl salts {e.g., alkyl pyridinium halides, alkyl quinolinium halides, alkyl indolinium halides, and the like), aliphatic heterocyclic salts (e.g., aliphatic heterocycloalkyl salts like alkyl piperidinium salts or aliphatic heterocycloalkenyl salts), aliphatic benzyl dialkyl ammoniums salts, dialiphatic dialkyl ammoniums salts, and tetraalkyl ammonium salts, and chloramine-T.

Amounts

The additives disclosed herein can be present in the disclosed antimicrobial compositions in any amount as is described herein for the individual ε-poly-L-lysine and quaternary ammonium compound components. Also by way of example, one or more additives can be present in an amount of from about 0.001 to about 0.1 weight %, from about 0.005 to about 0.075 weight %, from about 0.0075 about 0.05 weight %, from about 0.01 to about 0.02 weight %, about 0.005 to about 0.1 weight %, about 0.005 to about 0.02 weight %, about 0.005 to about 0.01 weight %, or about 0.01 weight %, based on the total weight of the antimicrobial composition. In another example, the disclosed antimicrobial compositions can contain from about 0.001 to about 0.1 parts by weight, from about 0.005 to about 0.075 parts by weight, from about 0.0075 about 0.05 parts by weight, from about 0.01 to about 0.02 parts by weight, about 0.005 to about 0.1 parts by weight, about 0.005 to about 0.02 parts by weight, about 0.005 to about 0.01 parts by weight, or about 0.01 parts by weight, based of one or more additives.

E. Sample Compositions And Embodiments

Other aspects and embodiments of this disclosure are provided. Reference is made to the Examples for illustrations of some exemplary compositions. In one embodiment, disclosed herein are antimicrobial compositions that comprise or consist essentially of E-polylysine and at least one of an aliphatic heteroaryl salt, an aliphatic benzyl dialkyl ammonium salt, and a tetraalkyl ammonium salt, and a carrier such as water. In additional embodiments, disclosed herein are antimicrobial compositions that comprise or consist essentially of E-polylysine and an aliphatic heteroaryl salt, and a carrier such as water. In additional embodiments, disclosed herein are antimicrobial compositions that comprise or consist essentially of E-polylysine, an aliphatic heteroaryl salt, and at least one of an aliphatic benzyl dialkyl ammonium salt, a dialiphatic dialkyl ammonium salt, and a tetraalkyl ammonium salt. For example, a useful composition comprises or alternatively consists essentially of E-polylysine, an aliphatic heteroaryl salt, and water. "Consisting essentially of" is used herein to exclude additional components or the omission of components that would change the basic and novel characteristics of the composition. Thus, in each instance in which consists essentially of language is used, it is intended to recited that the antimicrobial composition comprises an antimicrobial component, the antimicrobial component consisting essentially of the recited E-polylysine and quaternary ammonium salt. Thus, the "consisting essentially of" transitional phrase is intended to apply to the E-polylysine, aliphatic heteroaryl salts, aliphatic benzyl dialkyl ammonium salts, dialiphatic dialkyl ammoniums salts, and/or tetraalkyl ammonium salts from the composition but not apply to other carriers, adjuvants, solubilizing and suspending agents, and additional components as described herein. The composition can also comprise water.

In and other example, disclosed herein are antimicrobial compositions that comprise E-polylysine and an aliphatic heteroaryl salt. Also disclosed herein are antimicrobial compositions that consist essentially of E-polylysine and an aliphatic heteroaryl salt. In one aspect, the antimicrobial composition does not contain aliphatic benzyl dialkyl ammonium salts, dialiphatic dialkyl ammoniums salt, and tetraalkyl ammonium salts. The composition can also comprise water.

In the disclosed compositions, the aliphatic heteroaryl salt can be any aliphatic heteroaryl salt disclosed herein, for example, an alkylpyridinium halide. Such as alkylpyridinium halide can comprise or alternatively be selected from cetylpyridinium chloride, cetylpyridinium bromide, or a mixture thereof. The aliphatic benzyl dialkyl ammonium salt can be any aliphatic benzyl dialkyl ammonium salt disclosed herein, for example, an alkyl dimethyl benzyl ammonium halide, an alkyl diethyl benzyl ammonium halide, an alkyl methylethyl benzyl ammonium halide, or a combination thereof. The dialiphatic dialkyl ammonium salt can be any dialiphatic dialkyl ammonium salt disclosed herein, for example, didodecyl dimethyl ammonium halide, dicetyl dimethyl ammonium halide, dilauryl dimethyl ammonium halide, dimyristyl dimethyl ammonium halide, distearyl dimethyl ammonium halide, diarachidyl dimethyl ammonium halide, and a combination thereof. Moreover, the tetraalkyl ammonium salt can be any tetraalkyl ammonium salt disclosed herein, for example, cetyl trimethyl ammonium halide, lauryl trimethyl ammonium halide, myristyl trimethyl ammonium halide, stearyl trimethyl ammonium halide, arachidyl trimethyl ammonium halide, cetyl triethyl ammonium halide, or a mixture thereof. The composition can contain any of these components and the E-polylysine in any of the amounts disclosed above.

In another aspect, disclosed herein are antimicrobial compositions that comprise E-polylysine and an aliphatic heteroaryl salt. Also disclosed herein are antimicrobial compositions that comprise E-polylysine; an aliphatic heteroaryl salt; and one other ammonium salt selected from the group consisting of an aliphatic benzyl dialkyl ammonium salt, a dialiphatic dialkyl ammonium salt, and a tetraalkyl ammonium salt. In these compositions, when the ammonium salt is the aliphatic benzyl dialkyl ammonium salt, the composition does not contain the dialiphatic dialkyl ammonium salt or the tetraalkyl ammonium salt. Also in these compositions, when the ammonium salt is the dialiphatic dialkyl ammonium salt, the composition does not contain the aliphatic benzyl dialkyl ammonium salt or the tetraalkyl ammonium salt. When the ammonium salt is the tetraalkyl ammonium salt, the composition does not contain the aliphatic benzyl dialkyl ammonium salt or the dialiphatic dialkyl ammonium salt.

Also disclosed are compositions that comprise an antimicrobial component consisting essentially of E-polylysine and an aliphatic heteroaryl salt. It is also contemplated that these compositions can further comprise water. Further, this disclosure provides for compositions that comprise an antimicrobial component consisting essentially of E-polylysine, an aliphatic heteroaryl salt, and an ammonium salt selected from the group consisting of an aliphatic benzyl dialkyl ammonium salt, a dialiphatic dialkyl ammonium salt, and a tetraalkyl ammonium salt. It is also contemplated that these compositions can further "comprise water.

In yet another aspect, disclosed herein are antimicrobial compositions that comprise E-polylysine, an aliphatic heteroaryl salt, and two ammonium salts selected from the group consisting of an aliphatic benzyl dialkyl ammonium salt, a dialiphatic dialkyl ammonium salt, and a tetraalkyl ammonium salt. It is contemplated that these compositions can further comprise water. As with the other compositions, the aliphatic heteroaryl salt component can be any aliphatic heteroaryl salt described above (e.g., an alkylpyridinium halide such as cetylpyridinium chloride, cetylpyridinium bromide, or a mixture thereof).

In a further aspect, disclosed herein are compositions that contain an aliphatic heteroaryl salt and E-polylysine. The amount of these components can be as described above. Still further, a suitable antimicrobial composition can contain E-polylysine, an aliphatic heteroaryl salt, and a tetraalkyl ammonium salt. The amount of these components in the composition can be as described above.

In and other example, disclosed herein are antimicrobial compositions that comprise an aliphatic benzyl dialkyl ammonium salt and E-polylysine. For examples, disclosed herein are antimicrobial compositions that consist essentially of an aliphatic benzyl dialkyl ammonium salt and E-polylysine. In one aspect, the antimicrobial composition does not contain aliphatic heteroaryl salts, dialiphatic dialkyl ammonium salt, and tetraalkyl ammonium salts. The composition can also comprise water.

In the disclosed compositions, the aliphatic benzyl dialkyl ammonium salt can be any aliphatic benzyl dialkyl ammonium salt disclosed herein, for example, an alkyl benzalkonium halide such as alkyl dimethyl benzyl ammonium chloride, which is a mixture of $C_{12}$-$C_{18}$ alkyl dimethyl benzyl ammonium chloride, and alkyl methylethyl benzyl ammonium bromide, including mixtures thereof. The composition can contain the aliphatic benzyl dialkyl ammonium salt in any of the amounts disclosed above.

Aliphatic Heteroaryl Salt and E-polylysine Compositions

In one aspect, the antimicrobial composition can comprise an aliphatic heteroaryl salt and E-polylysine in any of the amounts disclosed above. For example, the aliphatic heteroaryl salt and the E-polylysine, independently, can be present in an amount of from about 0.01 to about 15 weight %, about 0.1 to about 12 parts by weight, from about 2 to about 10 weight %, or from about 3.5 to about 8 weight %. In another aspect, the aliphatic heteroaryl salt and the E-polylysine, independently, can be present in an amount of from about 0.01 to about 15 parts by weight, about 0.1 to about 12 parts by weight, or from about 2 to about 10 parts by weight, or from about 3.5 to about 8 parts by weight. Optionally, the composition can comprise a dialiphatic dialkyl ammoniums salt, a tetraalkyl ammonium salt, and/or other additives as disclosed herein.

Aliphatic Benzyl Dialkyl Ammonium Salt and E-polylysine Compositions

In one aspect, the antimicrobial composition can comprise an aliphatic benzyl dialkyl ammonium salt and E-polylysine in any of the amounts disclosed above. For example, the aliphatic benzyl dialkyl ammonium salt and the E-polylysine, independently, can be present in an amount of from about 0.01 to about 15 weight %, about 0.1 to about 12 weight %, from about 2 to about 10 weight %, or from about 3.5 to about 8 weight %. In another aspect, the aliphatic benzyl dialkyl ammonium salt and the E-polylysine, independently, can be present in an amount of from about 0.01 to about 15 parts by weight, about 0.1 to about 12 parts by weight, or from about 2 to about 10 parts by weight, or from about 3.5 to about 8 parts by weight. Optionally, the composition can comprise a dialiphatic dialkyl ammoniums salt, a tetraalkyl ammonium salt, and/or other additives as disclosed herein.

Aliphatic Heteroaryl Salt, Aliphatic Benzyl Dialkyl Ammonium Salt, and E-polylysine Compositions In one aspect, the antimicrobial composition can comprise an aliphatic heteroaryl salt, an aliphatic benzyl dialkyl ammonium salt, and E-polylysine in any of the amounts disclosed above. For example, the aliphatic heteroaryl salt, the aliphatic benzyl dialkyl ammonium salt, and the E-polylysine, independently, can be present in an amount of from about 0.01 to about 15 weight %, about 0.1 to about 12 weight %, from about 2 to about 10 weight %, or from about 3.5 to about 8 weight %. In another aspect, the aliphatic heteroaryl salt, the aliphatic benzyl dialkyl ammonium salt, and the E-polylysine, independently, can be present in an amount of from about 0.01 to about 15 parts by weight, about 0.1 to about 12 parts by weight, or from about 2 to about 10 parts by weight, or from about 3.5 to about 8 parts by weight. Optionally, the composition can comprise a dialiphatic dialkyl ammoniums salt, a tetraalkyl ammonium salt, and/or other additives as disclosed herein.

F. Use of the Compositions in Poultry Processing

The disclosed methods can be used to treat microbial contamination in a variety of food, meat, poultry, fruit, and vegetable processing environments. In general, any surface on which one desires to prevent and/or reduce microbial growth, viability, or survival can be treated by the disclosed methods. By way of example of the use of the disclosed antimicrobial compositions, the disclosed compositions can be used to treat microorganisms on poultry during poultry processing as illustrated in the Figures. FIG. 1 is a flow chart showing the processing steps taken during poultry processing. With reference to FIG. 1, conveyor 100 is used to transport the poultry through various steps of the processing plant. At step 101 live birds brought in are loaded onto an automated conveyor belt at step 105. At step 110, live birds are exposed to electrical current; this stage is also known as stunning. The birds are stunned when their heads (primarily the comb) contact a saline solution in the bottom of the stunner through which an electrical current is surging. This jolt of electricity is not severe enough to permanently damage or kill the bird, but immobilize the bird and allow the body of the bird to become relaxed enough to allow for automated killing. With the birds still hanging upside down, and necks outstretched due to stunning, the birds are exsanguinated by an automated circular blade at step 115 of the process.

After the blood is removed from the poultry, at step 120, the bird is submerged in a large tank of circulating hot water (about 128 to about 134° F.; about 53 to about 57° C.) for about 2 minutes to loosen the feathers. This process is called "scalding." The feathers and skin of the bird come out of the scalding process saturated with water. This process is particularly susceptible to bacterial cross-contamination since the birds are immersed in a common bath. Next is the picking process 125, and head removal 130 are performed. The birds are then dropped off of the aerial conveyor system at hock cutter step 135.

The U.S. Department of Agriculture ("USDA") requires one quart of fresh water or recycled water to be added for each bird that enters the scald tank; thus, there is a continuous overflow of water from the scald tank. In one aspect (see FIG. 2), the scald tank is replenished with the rinsate from the spray system downstream with the antimicrobial solution at slightly less than full strength (e.g., 502 ppm) in order to decrease the cross-contamination of pathogenic bacteria in the scald tank. At start up each day, the scald tank can be treated after it is initially filled with fresh water with the disclosed compositions at full strength. This can assure treatment of birds that pass through the scald tank, prior to the spray system rinsate recycle process.

Referring again to FIG. 1, at step 135, the preen gland is removed and at step 140a venting machine cut around the vent or the anus of the bird, removing about two inches of any possible remaining fecal mater from the colon. A chlorinated water spray is utilized on this machine to keep any possible fecal material from contaminating the outside skin of the bird. The next machine is the eviscerator (step 145), which uses a spoon-like device to pull the internal organs out of the body cavity. This machine typically has a chlorinated water spray to keep any intestinal contents from coming into contact with the outside surface of the bird. This machine does not entirely remove the guts or "viscera" from the carcass, but gently drapes the "viscera package" onto the back of the bird where it can be viewed by USDA inspection personnel for possible diseases. After the USDA inspector has viewed the entire bird, including the viscera package, the viscera are removed from the carcass and fall into the same offal trough which has already received the preen gland, head, and neck.

In some plants, the gizzard, heart, and liver are harvested from the birds for human consumption (step 150). However, the majority of processors now just let these become part of the inedible material leaving the plant because they receive more money for those products in the animal feeds business than in the consumer market. After the viscera are dropped into the trough or "offal line" (step 155), the lungs are suctioned out of the body cavity and then enter the offal line. This fully eviscerated carcass hanging on the shackle line by the legs is commonly referred to as the WOG (whole carcass without giblets). The next two steps are cropper 160 and the neck breaker 165.

After USDA inspection and viscera removal, the inside and outside of the carcass are thoroughly washed (step 170). While the carcasses are still moving on an overhead conveyor system, they pass through at least one "inside/outside bird washer." This system is comprised of a stainless steel cabinet that is designed for automated washing of carcasses. Several gallons of water are used to clean each individual carcass, inside and out. All of the water used in these wash cabinets is directed to the offal line. Thus, the spent wash water, water which is continually used to rinse off the evisceration machinery, water from hand and knife washing stations, and fresh water as needed, is utilized to move the inedible material through the offal troughs and is deposited into the waste stream.

Figure 2:
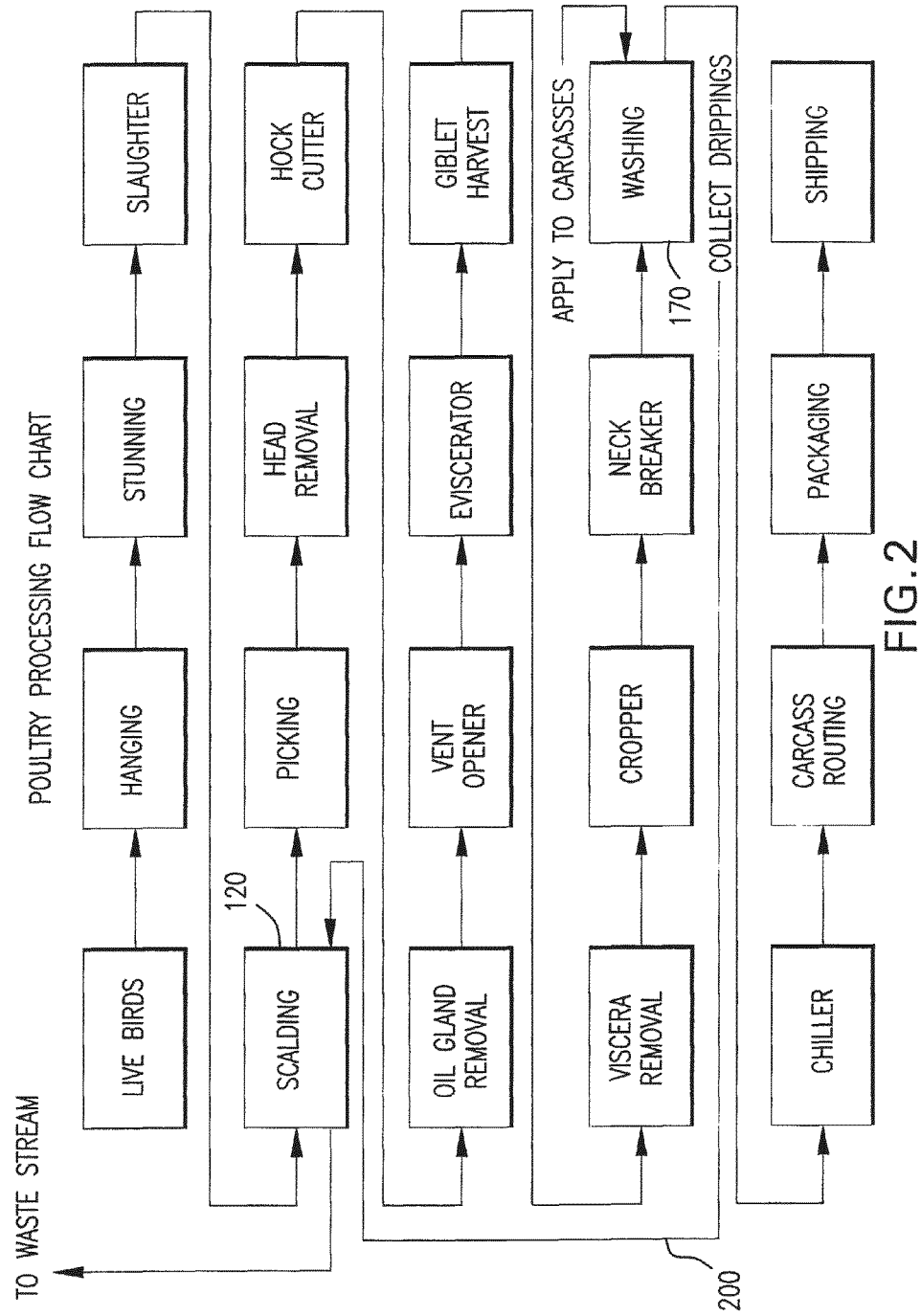
FIG. 2 is a flow chart showing a poultry processing method according to one aspect of the disclosed subject matter.

FIG. 2 is a flow chart showing a processing method according to one aspect of the subject matter disclosed herein. With reference to FIG. 2, the antimicrobial composition disclosed herein can be applied to the poultry at stage 170. This application is typically done by spraying the suspended poultry. The spraying process can include the outside as well as the insides of the poultry. During the spraying process, a predetermined amount of the antimicrobial composition is sprayed on the carcass. As shown in FIG. 2, the runoffs are then collected and supplied to the scalder for reuse. Thus, the antimicrobial composition along with fresh water are provided counter-current to the direction of the carcass. Thereafter, they may be reused in the scalder or added to the waste stream. If necessary, additional antimicrobial composition can be added to the recycled stream 200 in order to bring the concentration to the desired level. While the concentration may be varied depending on the application, it has been found that a concentration of about 200 to about 600 parts per million (ppm) of the disclosed compositions to water can be effective.

In another example, the process includes a first exposure of the poultry to the disclosed antimicrobial composition in the scalder (120). Filtered rinse-water from the antimicrobial spray positioned just prior to the chiller can be added to the fresh water entering the scalder at a concentration of about 450 to about 600 ppm (except for start-up where the initial scald tank water can be activated with the disclosed antimicrobial composition at full strength). This water can then pass over the carcasses and exit the scalder at the overflow (where carcasses enter the scalder). Thus, during the scalding step, the carcasses can be exposed to a maximum of about 450 to about 600 ppm of the disclosed antimicrobial composition. The carcasses can then continue down the processing line and through evisceration, cropping, and inside/outside bird washing, and finally pass through the spray cabinet, where a desired concentration of the disclosed antimicrobial composition can be applied again. The birds can then pass through the spray cabinet at normal line speed for application of the disclosed antimicrobial composition (e.g., about 0.2 gram of the antimicrobial solution per pound of carcass). Testing conducted by an independent laboratory showed that less than about 30 ppm of the antimicrobial composition disclosed herein remains on the carcass after both exposure points. That is, the majority of the disclosed antimicrobial composition drains out of the cabinet, is filtered, goes into the scalder, passes by the carcasses in the scalder and is sent to the waste stream. Material balance calculations demonstrate that about 99.9% of the disclosed antimicrobial composition will be sent to the waste stream.

In still another aspect, a drip tray can be included as part of the application system. As the birds exit the spray cabinet on their way to the chiller tank, they can pass over this drip tray, which collects any antimicrobial composition containing fluid that drips from the wet carcasses. This tray can extend for the distance covered by the carcasses in the first minute after they exit the spray cabinet, or typically about one-half the distance to the chiller. The liquid that drips into this tray can be combined with the fluid that drains from the antimicrobial spray cabinet and can be recycled back to the scalder. For the remainder of the distance to the chiller (i.e., the second minute of travel time from the spray cabinet), any liquid that drips from the carcasses can go into the plant's existing floor offal collection system and ultimately will be collected as part of the offal.

As indicated above, after treatment with the disclosed antimicrobial compositions, the carcasses can move via the overhead line to the chilling phase of the process. They drop automatically from the shackle line into a huge tank of water called the pre-chiller. This tank of water is typically held at about 55° F. (about 13° C.) and the carcasses remain in the pre-chiller for about 15 minutes. During this time, the carcasses absorb about 4 to about 5% added moisture. The water in the pre-chiller can be actively aerated to aid in water movement for increased chilling potential and water absorption. This aeration process, combined with the large amount of fat that is present in the pre-chill water, forms a flocculent material that floats on the top of the chill water. This material, typically called "chiller skimmings," is continuously removed from the pre-chiller water and diverted to the offal trough.

From the pre-chiller tank, the carcasses move into the chiller tank (shown as step 175 at FIG. 1). This tank is larger and colder than the pre-chiller, usually about 32 to about 34° F. (about 0 to about 1° C.). The carcasses stay in this tank for about 45 minutes, increasing their moisture content by an additional about 3 to about 4% in the chiller. USDA allows poultry carcasses to gain a total of 8% added moisture. Constant aeration of the water, combined with the fat that is present in the chiller water, forms a large amount of chiller skimmings. As is the case in the pre-chiller, this material is diverted to the offal trough. After chilling, the carcasses are rehung on a different shackle line for transport to other areas of the plant. They may move to a whole carcass packaging station (step 185), to cut-up or de-boning, or they may be shipped to a different plant for further processing and cooking (step 190).

The waste streams for antimicrobial solution in the poultry-processing environment are explained below. As stated, the great majority of the antimicrobial composition present in the spray solution can go to the scalder and, after passing through the scalder, can be conveyed to the waste stream and the offal. To achieve the desired concentration, additional antimicrobial solution can be added to the rinsate collected from the spray cabinet, prior to introduction into the scalder. Based upon calculations, the maximum concentration of antimicrobial solution that can enter the environment as a result of its intended use will be limited to the amount that remains in the water or combined with organic material after passing through the scalder and any residual that may drip from carcasses after spraying or be rinsed from the carcasses during chilling. (This amount has been calculated to be about 502 ppm of the antimicrobial solution residue on the carcass).

In one aspect, the antimicrobial solution can be applied by means of electrostatic coating. Use of an electrostatic sprayer can coat substantially all surfaces while requiring a minimal amount of material. Electrostatic spraying involves an electrostatic spray-charging system using air atomization, which can achieve a 1.6 to 24-fold increase in spray deposition over conventional application methods. Conventional methods for spraying chicken carcasses can require about 5 ozs. (about 148 mL) of sanitizer in order to be effective, whereas effectiveness using electrostatic spraying can require only about 0.3 ozs. (about 9 mL). Of course, the amount of the antimicrobial compositions disclosed herein will depend on the surface area to be treated, the composition concentration, and the like, as understood by one of skill in the art. Thus, application of the disclosed antimicrobial compositions using electrostatic spraying can significantly increase deposition and decrease the amount of product necessary to prevent microorganism growth and survival. Application of the disclosed antimicrobial compositions can be done after the reprocessing stage or in place thereof.

Figure 3:
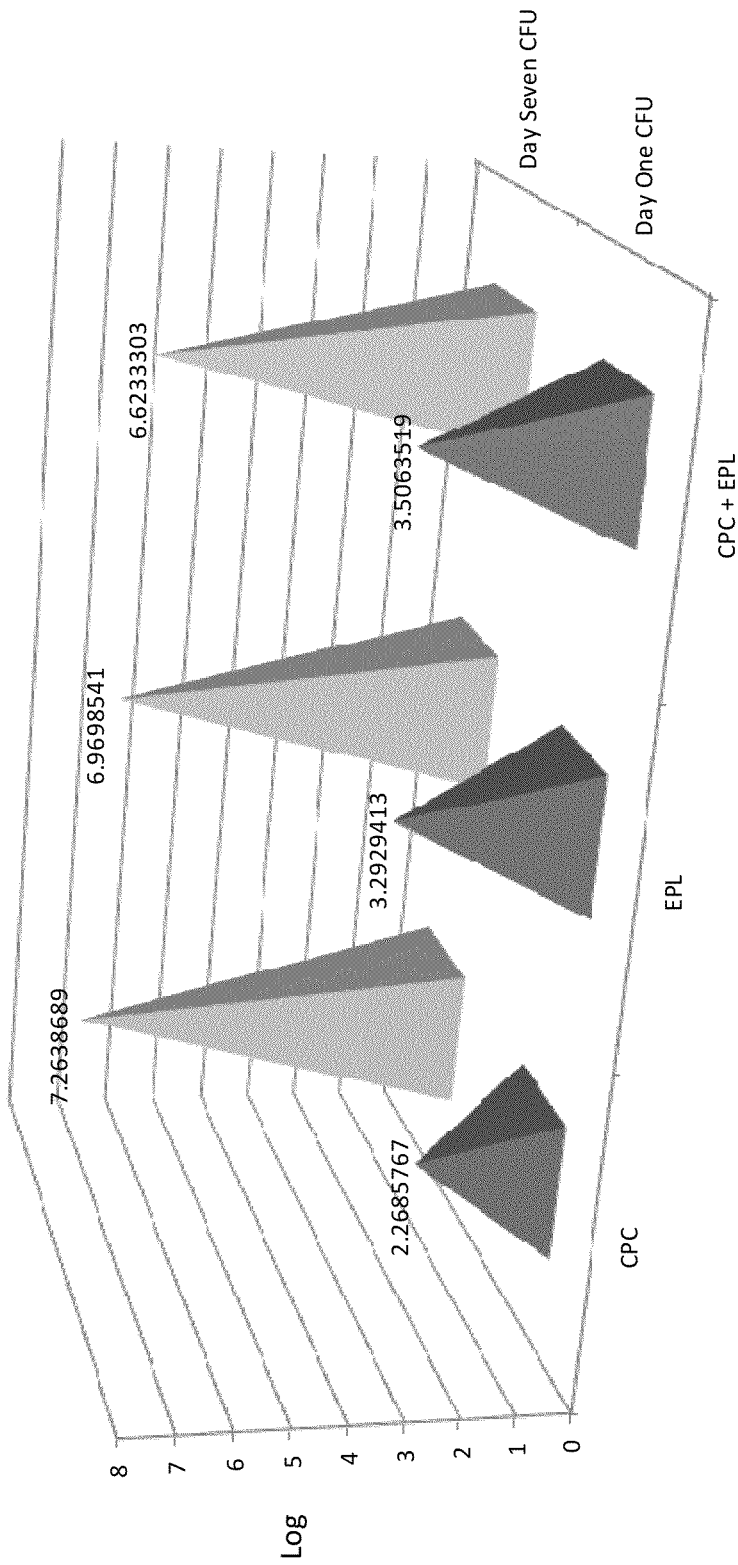
FIG. 3 compares the log averages for day 1 and day 7 CFUs (colony forming units) for samples treated with cetylpyridinium chloride (CPC) alone, epsilon-polylysine (EPL) alone, and a cetylpyridinium chloride and epsilon-polylysine combination (CPC+EPL) used as a blended and diluted finished product, as describe in the Examples.

Examples 1-3 and FIG. 3 present comparative data including the log averages for day 1 and day 7 CFUs (colony forming units) for poultry samples treated with cetylpyridinium chloride (CPC) only, epsilon-polylysine (EPL) only, as compared to a cetylpyridinium chloride and epsilon-polylysine combination (CPC+EPL) used as a blended product. As describe in the Examples, the CPC+EPL blended product is diluted from the concentrations of CPC and EPL used in the single component treatment to provide a diluted finished product.

Using the testing protocol described in the Examples, both day 1 and day 7 data for cetylpyridinium chloride only are presented in Table 1. These results for the CPC only test show an observed 4.9952922 log growth in yeast and mold, and 2 of 10 seven-day samples testing positive for *Salmonella*. Both day 1 and day 7 data for epsilon-polylysine only are presented in Table 2. These results for the EPL only test show an observed 3.6769128 log growth in yeast and mold, and 4 of 10 seven-day samples testing positive for *Salmonella*. The day 1 and day 7 data results for the CPC and EPL combination test using the diluted combination solution are presented in Table 3. These data show an observed 3.1169784 log growth in yeast and mold; 0 of 10 seven-day samples testing positive for *Salmonella*. These results are particularly noteworthy when it is understood that the solution used in the CPC and EPL combination test is some 27-fold diluted from a stock solution that contains both 1.0% CPC and 4.3% EPL, which would represent the simple additive combination of the Example 1 (CPC only) and the Example 2 (EPL only) antimicrobial components.

In FIG. 3, the differences between the day 1 and the day 7 CFUs for each respective sample illustrates their comparative performance, as does the substantially lower concentration of the CPC+EPL blend compared to the CPC and EPL individual samples needed to attain the smaller difference in the CPC+EPL blend samples. Thus, FIG. 3 plots the log averages for day 1 and day 7 CFUs (colony forming units) and demonstrates that even using the diluted CPC+EPL combination, the CPC+EPL combination tests showed some 1.8783138 (ca. 1.878) log lower growth in yeast and mold compared to the more concentrated CPC only tests. Similarly, using the diluted CPC+EPL combination, the CPC+EPL combination tests showed some 0.5599344 (ca. 0.560) log lower growth in yeast and mold compared to the more concentrated EPL only tests. Moreover, even though the CPC+EPL combination sample is substantially diluted from a simple composition that would represent the additive combination of these two individual components, no sample from the CPC+EPL combination tested positive for *Salmonella*, as compared to 20% and 40% of the more concentrated CPC only and EPL only samples, respectively. These results demonstrate that unexpectedly improved results for shelf life and antibacterial performance, including against *Salmonella*, are achieved using the combination of CPC and EPL, such that a much more dilute sample of the combined composition can be used to achieve even better performance that would be expected if the results were additive.

G. Additional Uses

Any surface can be treated by the methods and compositions disclosed herein. As such, the antimicrobial compositions disclosed herein have been found effective for applications other than treatment of poultry. For example, the disclosed antimicrobial compositions include treatment of other animal and vegetable tissue surfaces during processing, such as meat, pork, seafood, vegetables, legumes, fruit, and the like. Moreover, the present compositions can be retained on the animal and vegetable tissue surface after application, which significantly extends the shelf life of the animal and vegetable tissue. This latter effect provides a tremendous advantage producing, shipping, storing and selling such meat, pork, seafood, vegetables, legumes, and fruit products, especially when the quaternary ammonium compound is an aliphatic heteroaryl salt such as cetylpyridinium chloride, cetylpyridinium bromide, or a combination thereof.

Additionally, other surfaces that can be treated by the disclosed antimicrobial compositions include, but are not limited to, food processing equipment surfaces such as tanks, conveyors, floors, drains, coolers, freezers, equipment surfaces, walls, valves, belts, pipes, joints, crevasses, combinations thereof, and the like. The surfaces can be metal, for example, aluminum, steel, stainless steel, chrome, titanium, iron, alloys thereof, and the like. The surfaces can also be plastic, for example, polyolefins (e.g., polyethylene, polypropylene, polystyrene, poly(meth)acrylate, acrylonitrile, butadiene, ABS, acrylonitrile butadiene, etc.), polyester (e.g., polyethylene terephthalate, etc.), and polyamide (e.g., nylon), combinations thereof, and the like. The surfaces can also be brick, tile, ceramic, porcelain, wood, vinyl, linoleum, or carpet, combinations thereof, and the like. The surfaces can also, in other aspects, be food, for example, beef, poultry, pork, vegetables, legumes, fruits, seafood, crops, combinations thereof, and the like.

H. Forms

Depending on the intended mode of use, as is discussed below, the antimicrobial compositions disclosed herein can be in the form of solid, semi-solid, liquid, or gel forms, such as, for example, tablets, pills, capsules, powders, liquids, suspensions, dispersions, or emulsions. Also, the compositions disclosed herein can be in a form suitable for dilution. That is, the compositions can be in the form of an aqueous or non-aqueous stock solution, concentrate, concentrated solution, dispersion, emulsion, or suspension that can be diluted to a desired concentration with a suitable solvent (e.g., water). Similarly, the compositions can be in the form of a powder, paste, cream, or solid that can be reconstituted or mixed with a solvent and diluted to a desired concentration to form a solution or dispersion, emulsion, emulsifiable concentrated, slurries, or suspension. In one example, the disclosed antimicrobial compositions can be in the form of a solution, such as an aqueous solution.

It has been found that the disclosed antimicrobial compositions are equally effective even when concentrated or when diluted with water up to a certain point. For example, it has been found that the disclosed antimicrobial compositions can be diluted with water in the range of about 1 to about 1000 parts water to one part antimicrobial composition and still perform effectively. In some specific examples, the antimicrobial compositions disclosed herein can be diluted with water in a ratio of about 1:1, 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 21:1, 22:1, 23:1, 24:1, 25:1, 26:1, 27:1, 28:1, 29:1, 30:1, 31:1, 32:1, 33:1, 34:1, 35:1, 36:1, 37:1, 38:1, 39:1, 40:1, 41:1, 42:1, 43:1, 44:1, 45:1, 46:1, 47:1, 48:1, 49:1, 50:1, 51:1, 52:1, 53:1, 54:1, 55:1, 56:1, 57:1, 58:1, 59:1, 60:1, 61:1, 62:1, 63:1, 64:1, 65:1, 66:1, 67:1, 68:1, 69:1, 70:1, 71:1, 72:1, 73:1, 74:1, 75:1, 76:1, 77:1, 78:1, 79:1, 80:1, 81:1, 82:1, 83:1, 84:1, 85:1, 86:1, 87:1, 88:1, 89:1, 90:1, 91:1, 92:1, 93:1, 94:1, 95:1, 96:1, 97:1, 98:1, 99:1, 100:1, 101:1, 102:1, 103:1, 104:1, 105:1, 106:1, 107:1, 108:1, 109:1, 110:1, 111:1, 112:1, 113:1, 114:1, 115:1, 116:1, 117:1, 118:1, 119:1, 120:1, 121:1, 122:1, 123:1, 124:1, 125:1, 126:1, 127:1, 128:1, 129:1, 130:1, 131:1, 132:1, 133:1, 134:1, 135:1, 136:1, 137:1, 138:1, 139:1, 140:1, 141:1, 142:1, 143:1, 144:1, 145:1, 146:1, 147:1, 148:1, 149:1, 150:1, 151:1, 152:1, 153:1, 154:1, 155:1, 156:1, 157:1, 158:1, 159:1, 160:1, 161:1, 162:1, 163:1, 164:1, 165:1, 166:1, 167:1, 168:1, 169:1, 170:1, 171:1, 172:1, 173:1, 174:1, 175:1, 176:1, 177:1, 178:1, 179:1, 180:1, 181:1, 182:1, 183:1, 184:1, 185:1, 186:1, 187:1, 188:1, 189:1, 190:1, 191:1, 192:1, 193:1, 194:1, 195:1, 196:1, 197:1, 198:1, 199:1, 200:1, 201:1, 202:1, 203:1, 204:1, 205:1, 206:1, 207:1, 208:1, 209:1, 210:1, 211:1, 212:1, 213:1, 214:1, 215:1, 216:1, 217:1, 218:1, 219:1, 220:1, 221:1, 222:1, 223:1, 224:1, 225:1, 226:1, 227:1, 228:1, 229:1, 230:1, 231:1, 232:1, 233:1, 234:1, 235:1, 236:1, 237:1, 238:1, 239:1, 240:1, 241:1, 242:1, 243:1, 244:1, 245:1, 246:1, 247:1, 248:1, 249:1, 250:1, 251:1, 252:1, 253:1, 254:1, 255:1, 256:1, 257:1, 258:1, 259:1, 260:1, 261:1, 262:1, 263:1, 264:1, 265:1, 266:1, 267:1, 268:1, 269:1, 270:1, 271:1, 272:1, 273:1, 274:1, 275:1, 276:1, 277:1, 278:1, 279:1, 280:1, 281:1, 282:1, 283:1, 284:1, 285:1, 286:1, 287:1, 288:1, 289:1, 290:1, 291:1, 292:1, 293:1, 294:1, 295:1, 296:1, 297:1, 298:1, 299:1, 300:1, 301:1, 302:1, 303:1, 304:1, 305:1, 306:1, 307:1, 308:1, 309:1, 310:1, 311:1, 312:1, 313:1, 314:1, 315:1, 316:1, 317:1, 318:1, 319:1, 320:1, 321:1, 322:1, 323:1, 324:1, 325:1, 326:1, 327:1, 328:1, 329:1, 330:1, 331:1, 332:1, 333:1, 334:1, 335:1, 336:1, 337:1, 338:1, 339:1, 340:1, 341:1, 342:1, 343:1, 344:1, 345:1, 346:1, 347:1, 348:1, 349:1, 350:1, 351:1, 352:1, 353:1, 354:1, 355:1, 356:1, 357:1, 358:1, 359:1, 360:1, 361:1, 362:1, 363:1, 364:1, 365:1, 366:1, 367:1, 368:1, 369:1, 370:1, 371:1, 372:1, 373:1, 374:1, 375:1, 376:1, 377:1, 378:1, 379:1, 380:1, 381:1, 382:1, 383:1, 384:1, 385:1, 386:1, 387:1, 388:1, 389:1, 390:1, 391:1, 392:1, 393:1, 394:1, 395:1, 396:1, 397:1, 398:1, 399:1, 400:1, 450:1, 500:1, 550:1, 600:1, 650:1, 700:1, 750:1, 800:1, 850:1, 900:1, 950:1, or 1000:1, parts water to parts antimicrobial composition; these ratios can also be an upper and lower endpoint of a range of ratios when appropriate.

I. Methods of Making

Certain materials, compounds, compositions, and components disclosed herein can be obtained commercially or can be readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Alternatively, the components used in the antimicrobial compositions disclosed herein can be purchased from commercial suppliers.

The disclosed antimicrobial compositions can be prepared by admixing, in any order, E-polylysine, an aliphatic heteroaryl salt, and one or more of an aliphatic benzyl dialkyl ammonium salt, a dialiphatic dialkyl ammonium salt, and a tetraalkyl ammonium salt, and any optional additional components. Also, disclosed is an antimicrobial composition prepared by such a method. The resulting composition can also be diluted as described herein.

All publications and patents mentioned in this disclosure are incorporated herein by reference in their entireties, for the purpose of describing and disclosing the constructs and methodologies which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior invention. The references disclosed are also individually and specifically incorporated by reference herein for the material contained in them that is discussed in the sentence in which the reference is relied upon.

Unless indicated otherwise, when a range of any type is disclosed or claimed, for example a range of the number of pH, weight ratios, weight percentages, temperatures, and the like, it is intended to disclose or claim individually each possible number that such a range could reasonably encompass, including any sub-ranges encompassed therein. For example, when describing a range of weight percentages from about 1 to about 10 weight percent, each possible individual weight percentage value and combinations of ranges between these values are encompassed therein. For example, when disclosing a range of weight percentages from about 1 to about 5, Applicants' intent is to recite that weight percentage can be about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, about 4.0, and about 5.0, and these methods of describing such a range are interchangeable. When describing a range of measurements such as pH or temperature, every possible number that such a range could reasonably encompass typically refers to values within the range with one significant digit more than is present in the end points of a range.

Moreover, when a range of values is disclosed or claimed, which Applicants intent to reflect individually each possible number that such a range could reasonably encompass, Applicants also intend for the disclosure of a range to reflect, and be interchangeable with, disclosing any and all sub-ranges and combinations of sub-ranges encompassed therein. In this aspect, for example, Applicants' disclosure of a range of pH from about 6 to about 9, Applicants' disclosure is intended to literally encompass a pH of, for example, from about 6 to about 8.4, from about 7.2 to about 7.9, from about 6.5 to about 9, any combination of these ranges, and the like. Accordingly, Applicants reserve the right to proviso out or exclude any individual members of any such group, including any sub-ranges or combinations of sub-ranges within the group, if for any reason Applicants choose to claim less than the full measure of the disclosure, for example, to account for a reference that Applicants are unaware of at the time of the filing of the application.

In any application before the United States Patent and Trademark Office, the Abstract of this application is provided for the purpose of satisfying the requirements of 37 C.F.R. §1.72 and the purpose stated in 37 C.F.R. §1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that are employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

For any particular compound disclosed herein, the general structure presented is also intended to encompasses all conformational isomers and stereoisomers that can arise from a particular set of substituents, unless indicated otherwise. Thus, the general structure encompasses all enantiomers, diastereomers, and other optical isomers whether in enantiomeric or racemic forms, as well as mixtures of stereoisomers, as the context permits or requires. For any particular formula that is presented, any general formula presented also encompasses all conformational isomers, regioisomers, and stereoisomers that can arise from a particular set of substituents.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, may suggest themselves to one of ordinary skill in the art without departing from the spirit of the present invention or the scope of the appended claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Examples 1-3

Protocol for Comparison of $\epsilon$-Poly-L-Lysine and Quaternary Ammonium Compound Antimicrobial Properties Alone and in Combination The following solutions were prepared. A cetylpyridinium chloride (CPC) solution was prepared by combining 1.0 g of cetylpyridinium chloride (CAS No. 123-03-05) in 100 mL of water to form a nominal 1.0 wt % CPC test solution. An epsilon-polylysine (EPL) solution was prepared by combining 4.3 g epsilon-polylysine (CAS No. 25104-18-1) in water to form 100 mL of aqueous solution to form a nominal 4.3 wt % EPL test solution. The combination test solution was prepared by combining 1.0 g of cetylpyridinium chloride and 4.3 g epsilon-polylysine in water to form 100 mL of aqueous solution to form a standard concentration combination solution, and 3.7 g of this standard concentration solution was diluted up to 100 mL to form a combination test solution, which is diluted roughly 27-fold from the from the standard concentration solution.

The following test method was used. Whole poultry carcasses were collected from the processing line following evisceration and rinse. The carcasses were then treated with the CPC, EPL, or combined CPC+EPL products and dilution rates as listed above, using a Lillard spray application for 5 seconds. Following 10 seconds of dwell time, a 25 gram sample of the product was collected and immediately tested to establish a control sample set-point, and 325 grams of the same carcass were incubated at 37° C. for 168 hours (7 days). Following the incubation cycle, a second 25 gram sample was collected from the 325 gram control for testing evaluation of yeast and mold growth. A second 25 gram composite sample was collected from the same 325 gram control for pathogenic testing for *salmonella* presence. All samples were tested using AOAC accredited methods in an AOAC accredited API examined laboratory. Confirmation (split) samples were processed at ABC Research Laboratory.

It is demonstrated in the Examples 1-3 and Table 1-3 data that use of epsilon-polylysine and cetylpyridinium chloride as described above resulted in colony forming unit log growth rates of 3.6769128 and 4.9952922, respectively, after 7 days of incubation. Additionally, *salmonella* prevalence rates of 40% and 20%, for epsilon-polylysine and cetylpyridinium chloride, respectively, were noted following USDA/AOAC whole carcass rinse testing after the 7 day incubation process. Using the epsilon-polylysine and cetylpyridinium chloride combination blended as diluted finished product, the colony forming unit log growth rate of yeast and mold following 7 days of incubation was 3.1169784, which represents a −1.8783138 log difference in growth as compared to cetylpyridinium chloride alone and a −0.5599344 log difference in growth as compared to epsilon-polylysine alone. In addition, no product samples using the CPC+EPL blended finished product yielded positive *salmonella* results.

Example 1

Antimicrobial Tests Using Cetylpyridinium Chloride (CPC) Only

Using the testing protocol described above, both day 1 and day 7 data for cetylpyridinium chloride were collected analyzed, with the results presented in Table 1. These results for the CPC only test show an observed 4.9952922 log growth in yeast and mold, and 2 of 10 seven-day samples testing positive for *Salmonella*. These results are compared to the Examples 2 and 3 results in FIG. 3. In FIG. 3, the log averages for day 1 and day 7 CFUs (colony forming units) are shown.

TABLE 1

Antimicrobial tests using cetylpyridinium chloride (1.0%), day 1 versus day 7

| | CPC Day 7 | | | | CPC Day 1 | | | |
|---|---|---|---|---|---|---|---|---|
| Test | CFU | Log | Log Avg | *Salmonella* | Cntrl | CFU | Log | Log Avg |
| 1 | 14400000 | 7.1583625 | 7.2638689 | POSITIVE | 1 | 90 | 1.9542425 | 2.2685767 |
| 2 | 20800000 | 7.3180633 | | NEGATIVE | 2 | 170 | 2.2304489 | |
| 3 | 216000000 | 8.3344538 | | NEGATIVE | 3 | 1000 | 3 | |
| 4 | 23600000 | 7.372912 | | NEGATIVE | 4 | 480 | 2.6812412 | |
| 5 | 20800000 | 7.3180633 | | NEGATIVE | 5 | 540 | 2.7323938 | |
| 6 | 20400000 | 7.3096302 | | NEGATIVE | 6 | 120 | 2.0791812 | |
| 7 | 6400000 | 6.80618 | | NEGATIVE | 7 | 130 | 2.1139434 | |
| 8 | 8000000 | 6.90309 | | POSITIVE | 8 | 70 | 1.845098 | |
| 9 | 16400000 | 7.2148438 | | NEGATIVE | 9 | 280 | 2.447158 | |
| 10 | 8000000 | 6.90309 | | NEGATIVE | 10 | 40 | 1.60206 | |

Results for CPC (1.0%) only: 4.9952922 log growth in yeast and mold over 7 days; 2 of 10 seven-day samples tested positive for *Salmonella*.

Example 2

Antimicrobial Tests Using ε-Poly-L-Lysine (Epsilon-Polylysine or EPL) Only

Using the testing protocol described above, both day 1 and day 7 data for epsilon-polylysine were collected analyzed, with the results presented in Table 2. These results for the EPL only test show an observed 3.6769128 log growth in yeast and mold, and 4 of 10 seven-day samples testing positive for *Salmonella*. These results are compared to the Examples 1 and 3 results in FIG. 3. In FIG. 3, the log averages for day 1 and day 7 CFUs (colony forming units) are shown.

TABLE 2

Antimicrobial tests using ε-poly-L-lysine (4.3%), day 1 versus day 7

| | EPL Day 7 | | | | EPL Day 1 | | | |
|---|---|---|---|---|---|---|---|---|
| Test | CFU | Log | Log Avg | *Salmonella* | Cntrl | CFU | Log | Log Avg |
| 1 | 4200000 | 6.6232493 | 6.9698541 | *Salmonella* | 1 | 1560 | 3.1931246 | 3.2929413 |
| 2 | 12400000 | 7.0934217 | | NEGATIVE | 2 | 3400 | 3.5314789 | |
| 3 | 4700000 | 6.6720979 | | POSITIVE | 3 | 2120 | 3.3263359 | |
| 4 | 11200000 | 7.049218 | | POSITIVE | 4 | 970 | 2.9867717 | |
| 5 | 5200000 | 6.7160033 | | NEGATIVE | 5 | 1250 | 3.09691 | |
| 6 | 4400000 | 6.6434527 | | POSITIVE | 6 | 3200 | 3.50515 | |
| 7 | 19800000 | 7.2966652 | | NEGATIVE | 7 | 3000 | 3.4771213 | |
| 8 | 18900000 | 7.2764618 | | NEGATIVE | 8 | 3000 | 3.4771213 | |
| 9 | 11200000 | 7.049218 | | POSITIVE | 9 | 720 | 2.8573325 | |
| 10 | 19000000 | 7.2787536 | | NEGATIVE | 10 | 3000 | 3.4771213 | |

Results for EPL (4.3%) only: 3.6769128 log growth in yeast and mold over 7 days; 4 of 10 seven-day samples tested positive for *Salmonella*.

Example 3

Antimicrobial Tests Using Cetylpyridinium Chloride (CPC) and ε-Poly-L-Lysine (EPL) in Combination

Using the testing protocol described above, both day 1 and day 7 data for epsilon-polylysine were collected analyzed, with the results presented in Table 3. These results for the CPC and EPL combination test show an observed 3.1169784 log growth in yeast and mold; 0 of 10 seven-day samples testing positive for *Salmonella*. These results are compared to the Examples 2 and 3 results in FIG. 3, and are particularly noteworthy when it is understood that the solution used in the CPC and EPL combination test is some 27-fold diluted from a stock solution that contains both 1.0% CPC and 4.3% EPL, which would represent the simple additive combination of the Example 1 and the Example 2 antimicrobial components. FIG. 3 plots the log averages for day 1 and day 7 CFUs (colony forming units). Thus, even using the diluted CPC+ EPL combination, the CPC+EPL combination tests showed some 1.8783138 (ca. 1.878) log growth reduction in yeast and mold compared to the more concentrated CPC only tests. Similarly, using the diluted CPC+EPL combination, the CPC+EPL combination tests showed some 0.5599344 (ca. 0.560) log growth reduction in yeast and mold compared to the more concentrated EPL only tests.

Moreover, even using the diluted CPC+EPL combination, no sample tested positive for *Salmonella*, as compared to 20% and 40% of the more concentrated CPC only and EPL only samples, respectively. These results demonstrate that unexpectedly improved results for shelf life and antibacterial performance including against *Salmonella*, are achieved using the combination of CPC and EPL, such that a much more dilute sample of the combined composition can be used to achieve even better performance that would be expected if the results were additive.

TABLE 3

Antimicrobial tests using a diluted cetylpyridinium chloride and epsilon-polylysine combination solution, day 1 versus day 7

| | Day 7 | | | | | Day 1 | | |
| --- | --- | --- | --- | --- | --- | --- | --- | --- |
| Test | CFU | Log | Log Avg | *Salmonella* | Cntrl | CFU | Log | Log Avg |
| 1 | 3600000 | 6.5563025 | 6.6233303 | NEGATIVE | 1 | 4100 | 3.6127839 | 3.5063519 |
| 2 | 5200000 | 6.7160033 | | NEGATIVE | 2 | 3200 | 3.50515 | |
| 3 | 1500000 | 6.1760913 | | NEGATIVE | 3 | 1700 | 3.2304489 | |
| 4 | 7600000 | 6.8808136 | | NEGATIVE | 4 | 3000 | 3.4771213 | |
| 5 | 3100000 | 6.4913617 | | NEGATIVE | 5 | 5200 | 3.7160033 | |
| 6 | 7200000 | 6.8573325 | | NEGATIVE | 6 | 3000 | 3.4771213 | |
| 7 | 6600000 | 6.8195439 | | NEGATIVE | 7 | 3200 | 3.50515 | |
| 8 | 4200000 | 6.6232493 | | NEGATIVE | 8 | 3000 | 3.4771213 | |
| 9 | 2700000 | 6.4313638 | | NEGATIVE | 9 | 3300 | 3.5185139 | |
| 10 | 4800000 | 6.6812412 | | NEGATIVE | 10 | 3500 | 3.544068 | |

Results for CPC (4.3%) solution + EPL (1.0%) solution, with combination solution diluted to 3.7%: 3.1169784 log growth in yeast and mold over 7 days; 0 of 10 seven-day samples tested positive for *Salmonella*.

These results, using yeast and mold bacterium growth as an indicator, suggest that the synergistic effect of combining epsilon-polylysine and cetylpyridinium chloride would increase consumer food product shelf stability as well as remediate pathogenic growth.

Example 4

Sample Formulations

Exemplary formulations according to this disclosure, using a variety of GRAS (Generally Recognized As Safe) components is provided in the following Table 4. The balance of the formulation can be water or can be water in combination with the additional components disclosed herein.

TABLE 4

Exemplary formulations

| | | | Amount[4] | | | |
| --- | --- | --- | --- | --- | --- | --- |
| Formulation | CPC | EPL | Nisin | EDTA | APG | Lactic Acid |
| 1 | 0-500 ppm | 0-600 ppm | 0.05-5% | 0.05-5% | 0.05-1% | 0.1-5% |
| 2 | 500 ppm | 600 ppm | — | — | — | — |
| 3 | 250 ppm | 600 ppm | — | — | — | — |
| 4 | 250-500 ppm | 600 ppm | — | — | — | — |
| 5 | 50-500 ppm | 100-600 ppm | 0.1-5% | — | — | — |
| 6 | 50-500 ppm | 100-600 ppm | — | 0.1-5% | — | — |
| 7 | 50-500 ppm | 100-600 ppm | — | — | 0.1-1% | — |
| 8 | 50-500 ppm | 100-600 ppm | — | — | — | 0.1-5% |
| 9 | 500 ppm | 600 ppm | 500 ppm | 500 ppm | — | — |

TABLE 4-continued

Exemplary formulations

| Formulation | CPC | | EPL | | Nisin | EDTA | APG | Lactic Acid |
|---|---|---|---|---|---|---|---|---|
| 10 | 1-2000 | ppm | 1-3500 | ppm | 0-5% | 0-5% | 0-3% | 0-5% |
| 11 | 1-2000 | ppm | 1-3500 | ppm | 0.1-5% | — | — | — |
| 12 | 1-2000 | ppm | 1-3500 | ppm | — | 0.1-5% | — | — |
| 13 | 1-2000 | ppm | 1-3500 | ppm | — | — | 0.1-1% | — |
| 14 | 1-2000 | ppm | 1-3500 | ppm | — | — | — | 0.1-5% |
| 15 | 50-800 | ppm | 200-2000 | ppm | 0-5% | 0-5% | 0-3% | 0-5% |
| 16 | 50-800 | ppm | 200-2000 | ppm | 0.1-5% | — | — | — |
| 17 | 50-800 | ppm | 200-2000 | ppm | — | 0.1-5% | — | — |
| 18 | 50-800 | ppm | 200-2000 | ppm | — | — | 0.1-1% | — |
| 19 | 50-800 | ppm | 200-2000 | ppm | — | — | — | 0.1-5% |
| 20 | 100-800 | ppm | 250-3000 | ppm | 0-5% | 0-5% | 0-4% | 0-5% |
| 21 | 200-600 | ppm | 500-2500 | ppm | 0-5% | 0-5% | 0-5% | 0-5% |
| 22 | 250-500 | ppm | 800-2250 | ppm | 0-5% | 0-5% | 0-5% | 0-5% |
| 23 | 250-500 | ppm | 1000-2000 | ppm | 0.1-5% | — | — | — |
| 24 | 300-750 | ppm | 1200-1800 | ppm | — | 0.1-5% | — | — |
| 25 | 300-600 | ppm | 1500-1700 | ppm | — | — | 0.1-1% | — |
| 26 | 200-500 | ppm | 500-1000 | ppm | — | — | — | 0.1-5% |
| 27 | 400-650 | ppm | 700-1250 | ppm | 0-5% | 0-5% | 0-4% | 0-5% |
| 28 | 100 | ppm | 1000 | ppm | — | — | — | — |
| 29 | 200 | ppm | 1100 | ppm | — | — | — | — |
| 30 | 300 | ppm | 1200 | ppm | — | — | — | — |
| 31 | 400 | ppm | 1300 | ppm | — | — | — | — |
| 32 | 500 | ppm | 1500 | ppm | — | — | — | — |
| 33 | 1000-2000 | ppm | 250-500 | ppm | — | — | — | — |
| 34 | 1200-1800 | ppm | 300-750 | ppm | — | — | — | — |
| 35 | 1500-1700 | ppm | 300-600 | ppm | — | — | — | — |
| 36 | 500-1000 | ppm | 200-500 | ppm | — | — | — | — |
| 37 | 700-1250 | ppm | 400-650 | ppm | — | — | — | — |

[4]CPC, cetypyridinium chloride; EPL, ε-poly-L-lysine; EDTA, ethylenediamine tetraacetic acid; APG, alkyl polyglucoside.

The formulations in the table are exemplary and not intending to be limiting, and any single or multiple component in each formulation listed can be used in the concentration or amount disclosed in the specification. Therefore, in one aspect, this disclosure provides for an antimicrobial composition comprising:
a) at least one GRAS (generally recognized as safe) component selected from ε-poly-L-lysine, Nisin, EDTA, alkyl polyglucoside, lactic acid, or any combination thereof; and
b) at least one quaternary ammonium compound.
Generally, this composition further comprises water, but also can comprise the other recited additives as disclosed herein. By way of example, one preferred formulation comprises or consists essentially of ε-poly-L-lysine, Nisin, EDTA, cetyl pyridinium chloride, and water.

It will also be understood by those of skill in the art that although the components of the exemplary embodiments are represented in their respective weight percent, the ratios may nonetheless be varied to include molar or volume percent of each component.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:
1. An antimicrobial composition comprising:
a) ε-poly-L-lysine; and
b) cetylpyridinium chloride;
wherein the ε-poly-L-lysine and the cetylpyridinium chloride are present in the composition in a weight ratio of from about 4:1.

2. An antimicrobial composition according to claim 1, wherein the ε-poly-L-lysine contains from about 20 to about 40 L-lysine residues.

3. An antimicrobial composition according to claim 1, further comprising water, wherein the ε-poly-L-lysine is present in the composition in a weight percentage of from 0.01 wt % to 15 wt %.

4. An antimicrobial composition according to claim 1, further comprising at least one additive selected independently from a carrier, a diluent, an adjuvant, a solubilizing agent, a suspending agent, a surfactant, a secondary antimicrobial agent, a preservative, a filler, a viscosity modifier, a thixotropy modifier, an antifoaming agent, a wetting agent, an emulsifier, or combinations thereof.

5. An antimicrobial composition according to claim 1, further comprising at least one surfactant selected from a cationic surfactant, an anionic surfactant, a non-ionic surfactant, and an amphoteric surfactant.

6. An antimicrobial composition, comprising:
a) a component having antimicrobial activity, consisting essentially of:
i) ε-poly-L-lysine; and
ii) cetylpyridinium chloride; and
b) an aqueous carrier;
wherein the ε-poly-L-lysine and the cetylpyridinium chloride are present in the composition in a weight ratio of from about 4:1.

7. A method for reducing the number of microorganisms on a surface, comprising contacting a surface with a composition according to claim 1.

8. A method for reducing the number of microorganisms on a surface according to claim 7, wherein the ε-poly-L-lysine contains from about 20 to about 40 L-lysine residues.

9. A method for reducing the number of microorganisms on a surface according to claim 7, wherein the surface is a poultry, meat, seafood, vegetables, legumes, fruit, food, or food processing equipment surface.

10. A method for reducing the number of microorganisms on a surface according to claim 7, wherein the microorganism comprises *Salmonella typhimurium, Aeromonas hydrophile, Arcobacter butzleri, Bacillus cereus, Campylobacter jejuni, Escherichia coli, Listeria monocytogenes, Staphylococcus aureus, Pseudomonas fluorescens*, or *Shewanella putrefaciens*.

11. An antimicrobial composition according to claim 1, further comprising water, wherein the ϵ-poly-L-lysine is present in the composition in a weight percentage of from 0.16 wt % to 4.3 wt %.

12. An antimicrobial composition according to claim 1, further comprising water, wherein the cetylpyridinium chloride is present in the composition in a weight percentage of from 0.01 wt % to 15 wt %.

13. An antimicrobial composition according to claim 1, further comprising water, wherein the cetylpyridinium chloride is present in the composition in a weight percentage of from 0.037 wt % to 1.0 wt %.

14. An antimicrobial composition according to claim 1, further comprising water, wherein the ϵ-poly-L-lysine is present in the composition in a weight percentage of from 0.16-4.3 wt % and the cetylpyridinium chloride is present in the composition in a weight percentage of from 0.037-1.0 wt %.

* * * * *